US009696299B2

(12) United States Patent
Guzman

(10) Patent No.: US 9,696,299 B2
(45) Date of Patent: *Jul. 4, 2017

(54) INTEGRATED MODULAR UNIT INCLUDING AN ANALYTE CONCENTRATOR MICROREACTOR DEVICE CONNECTED TO A CARTRIDGE-CASSETTE

(71) Applicant: Norberto Guzman, East Brunswick, NJ (US)

(72) Inventor: Norberto Guzman, East Brunswick, NJ (US)

( * ) Notice: Subject to any disclaimer, the term of this patent is extended or adjusted under 35 U.S.C. 154(b) by 68 days.

This patent is subject to a terminal disclaimer.

(21) Appl. No.: 14/561,855

(22) Filed: Dec. 5, 2014

(65) Prior Publication Data

US 2015/0093304 A1    Apr. 2, 2015

Related U.S. Application Data

(63) Continuation-in-part of application No. 14/258,406, filed on Apr. 22, 2014, now Pat. No. 9,482,602, (Continued)

(51) Int. Cl.
*G01N 27/00* (2006.01)
*G01N 33/53* (2006.01)
(Continued)

(52) U.S. Cl.
CPC ... *G01N 33/5302* (2013.01); *G01N 27/44743* (2013.01); *B01L 3/502715* (2013.01); *G01N 2001/4038* (2013.01)

(58) Field of Classification Search
CPC .. G01N 1/405; G01N 27/44743; G01N 33/53; G01N 33/5302; G01N 33/543;
(Continued)

(56) References Cited

U.S. PATENT DOCUMENTS 5,202,010 A    4/1993   Guzman
5,741,639 A    4/1998   Ensing et al.
(Continued)

OTHER PUBLICATIONS

Ramsey et al., "High-Efficiency, Two-Dimensional Separations of Protein Digests on Microfluidic Devices" Anal. Chem. 75:3758-3764 (2003).
(Continued)

*Primary Examiner* — Erik B Crawford
(74) *Attorney, Agent, or Firm* — Porzio, Bromberg, Newman P.C.

(57) ABSTRACT

The integrated modular and interchangeable unit of the present invention comprises an analyte concentrator-microreactor (ACM) device having four entrance-exit ports identified as connection areas to a transport capillary for sample and buffer introduction, and to a separation capillary of a cartridge-cassette filled with an appropriate separation fluid for optimal separation of the analytes of interest. Affinity ligand groups are immobilized to microstructures contained within the main inner cavity or channel of the device or directly to the wall of the main inner channel for capturing one or more analytes. The inlet and outlet ends of the transport capillary are connected through a parallel design option to the analyte concentrator-microreactor (ACM) device to facilitate the path of sample and buffers through the inner cavity or channel of the analyte concentrator-microreactor (ACM) device.

55 Claims, 5 Drawing Sheets

Related U.S. Application Data which is a continuation of application No. 13/487,451, filed on Jun. 4, 2012, now Pat. No. 8,703,061, which is a continuation-in-part of application No. 13/284,087, filed on Oct. 28, 2011, now Pat. No. 8,865,075.

(60) Provisional application No. 61/492,521, filed on Jun. 2, 2011, provisional application No. 61/408,689, filed on Nov. 1, 2010.

(51) Int. Cl.
    *G01N 27/447* (2006.01)
    *B01L 3/00* (2006.01)
    *G01N 1/40* (2006.01)

(58) Field of Classification Search
    CPC ......... G01N 33/54313; B01L 3/502715; B01L 3/502753; B01L 9/527
    See application file for complete search history.

(56) References Cited

U.S. PATENT DOCUMENTS

| | | | |
|---|---|---|---|
| 5,800,692 | A | 9/1998 | Naylor et al. |
| 6,406,604 | B1 | 6/2002 | Guzman |
| 7,329,388 | B2 | 2/2008 | Guzman |
| 7,407,568 | B1 | 8/2008 | Malik et al. |
| 7,736,480 | B2 | 6/2010 | Guzman |
| 7,811,436 | B2 | 10/2010 | Guzman |
| 7,828,948 | B1 | 11/2010 | Hatch et al. |
| 7,959,861 | B2 | 6/2011 | Lopez et al. |
| 8,007,724 | B2 | 8/2011 | Guzman |
| 8,007,725 | B2 | 8/2011 | Guzman |
| 8,030,092 | B2 | 10/2011 | Guzman |
| 8,703,061 | B2 | 4/2014 | Guzman |
| 8,865,075 | B2 | 10/2014 | Guzman |
| 9,482,602 | B2 | 11/2016 | Guzman |

OTHER PUBLICATIONS

Guzman, N. A. "Improved solid-phase microextraction device for use in on-line immunoaffinity capillary electrophoresis" Electrophoresis 24:3718-3727 (2003).
Li et al. "Integration of Isoelectric Focusing with Parallel Sodium Dodecyl Sulfate Gel Electrophoresis for Multidimensional Protein Separations in a Plastic Microfludic Network" Anal. Chem. 76:742-748 (2004).
Guzman, N.A. "Immunoaffinity capillary electrophoresis applications of clinical and pharmaceutical relevance" Anal Bioanal Chem 378:37-39 (2004).
Ye et al., "On-line protein digestion and peptide mapping by capillary electrophoresis with post-column labeling for laser-induced fluorescence detection" Electrophoresis 25:1319-1326 (2004).
Renzi et al., "Hand-Held Microanalytical Instrument for Chip-Based Electrophoretic Separations of Proteins" Anal. Chem. 77:435-441 (2005).
Guzman et al., "Proteomics Studies—This 2-D separation technique can complement MS-based proteomics methods" Analytical Chemistry 61-67 (2005).
Kartalov et al., "High-throughput multi-antigen microfluidic fluorescence immunoassays" BioTechniques 40(1):85-90 (2006).
Mallik et al., "Affinity monolith chromatography" J. Sep. Sci. 29:1686-1704 (2006).
Nagrath et al."Isolation of rare circulating tumour cells in cancer patients by microchip technology" Nature 450 (20/27) 1235-1241 (2007).
Khurana et al. "Preconcentration, Separation, and Indirect Detection of Nonfluorescent Analytes Using Fluorescent Mobility Markers" Anal. Chem. 80:279-286 (2008).
Guzman et al., "Immunoaffinity capillary electrophoresis as a powerful strategy for the quantification of low-abundance biomarkers, drugs, and metabolites in biological matrices" Electrophoresis 29:3259-3278 (2008).
Chen et al. "Magnetic Beads Based Immunoaffinity Capillary Electrophoresis of Total Serum IgE with Laser-Induced Fluorescence Detection" Anal. Chem. 80:9583-9588 (2008).
Phillips et al., "Enrichment of Cancer Cells Using Aptamers Immobilized on a Microfluidic Channel" Anal. Chem. 81:1033-1039 (2009).
Yuen et al. "Multidimensional modular microfluidic system" Lab Chip, 9:3303-3305 (2009).
Phillips et al., "Immunoaffinity Techniques in Analysis" J Chromatogr B Analyt Technol Biomed Life Sci. 878(2):113 (2010).
Moser et al. "Immunoaffinity chromatography: an introduction to applications and recent developments" Bioanalysis. 2(4):769-790 (2010).
Dharmasiri et al. "Microsystems for the Capture of Low-Abundance Cells" Annu. Rev. Anal. Chem. 3:409-31 (2010).
Parker et al., "Mass-spectrometry-based clinical proteomics—a review and prospective" Analyst, 135:1830-1838 (2010).
Guzman et al., "Immunoaffinity capillary electrophoresis: A new versatile tool for determining protein biomarkers in inflammatory processes" Electrophoresis 32:1565-1578 (2011).
Hua et al., "On-chip solid phase extraction and enzyme digestion using cationic PolyE-323 coatings and porous polymer monoliths coupled to electrospray mass spectrometry" Journal of Chromatography A, 1218:4039-4044 (2011).
Wang et al., "Effect of Surface Nanotopography on Immunoaffinity Cell Capture in Microfluidic Devices" Langmuir 27:11229-11237 (2011).
Whiteaker et al., "Peptide Immunoaffinity Enrichment Coupled with Mass Spectrometry for Peptide and Protein Quantification" Clin Lab Med 31:385-396 (2011).

INTEGRATED MODULAR UNIT INCLUDING AN ANALYTE CONCENTRATOR MICROREACTOR DEVICE CONNECTED TO A CARTRIDGE-CASSETTE

CROSS-REFERENCE TO RELATED APPLICATION

This application is a continuation-in-part of U.S. patent application Ser. No. 14/258,406 filed Apr. 22, 2014, which is a continuation of U.S. patent application Ser. No. 13/487,451 filed Jun. 2, 2012, which claims the benefit of U.S. Provisional Patent Application No. 61/492,521 filed Jun. 2, 2011, which is a continuation-in-part of U.S. patent application Ser. No. 13/284,087 filed Oct. 28, 2011, which claims the benefit of U.S. Provisional Patent Application No. 61/408,689 filed Nov. 1, 2010, the entireties of all of which applications are hereby incorporated by reference into this application.

BACKGROUND OF THE INVENTION

Field of the Invention

The present invention relates generally to the analysis of chemical, biological, and cellular materials or structures and, more in particular, to a modified modular, portable and interchangeable analyte concentrator-microreactor (ACM) device, containing one or more immobilized affinity ligand groups, that can be coupled or mounted to a cartridge-cassette of a capillary electrophoresis apparatus or another similar unit of any other analytical separation apparatus. The analyte concentrator-microreactor (ACM) device is a functional and integral component of a cartridge-cassette of an analytical separation apparatus, to be used for the capture, isolation, purification, concentration, and release of simple and/or complex molecules, materials, and/or structures, as a whole or parts, to further be separated by a separation capillary or passage, followed by detection, quantification and characterization employing appropriate conditions for separation and the use of one or more detectors.

Description of Related Art

Microfabrication techniques have improved rapidly over the last decade, stimulated primarily by advancements in the microprocessor industry. Microfabrication in the field of analytical chemistry is having an impact on the manufacturing of small-sized analytical instrumentation and methods. Smaller-scale analysis often reduces requirements for reagents, electrical power and allows the manufacture of portable instruments that can be used in the field and in remote locations. Furthermore, microfabrication techniques facilitate the analysis of a sample in short periods of time, at high sensitivity, with high-throughput multi-dimensional/multi-task capabilities, environmental friendly, easy to operate and of interpreting the results, and being cost effective. Miniaturized platform technologies are one of the main challenges in medical device technology, in particular in the area of diagnostics. New and more versatile point-of-care diagnostic devices and methods are having an impact in the decentralization of diagnostics, helping to make disease diagnosis faster and more accurate, and facilitating decisions for an appropriate therapy and/or surgery if necessary. The increasing knowledge of the complex nature of molecular interactions has enabled not only a better understanding of physiological and pathological processes, but also the identification of biological markers (biomarkers) that define a particular state or condition.

Molecular and cellular biomarkers are now used across many disciplines and can be any molecule or cellular structure, part of a molecule or cellular structure, or even a particular configuration that is both detectable and measurable, where the amount, appearance or other property is indicative of a particular biological state. Typically diagnostic tests have been based on single biomarkers; however, basing a clinical decision on a single biomarker can lead to a significant level of false positives. As a consequence, multiplexing of biomarkers (e.g., signatures or panels) is being used to provide improved sensitivity, specificity and accuracy for the diagnosis and characterization of disease.

With the help of a panel of biomarkers it is possible to assess a disease at the very early stage of its formation, which is also helping in the understanding of how a selective treatment for a particular disease can work. The dogma is changing from using diagnostic tests mainly for diagnosing an advance stage of a disease, with defined symptoms, to a more predictive and pre-symptomatic analysis of a disease at an early stage of formation. There is a strong clinical imperative to identify discerning molecular biomarkers of disease that offer early detection of pathogenesis, inform prognosis, guide therapy, and monitor disease progression.

Therefore, there is an enduring need for improving instruments, technologies, and methodologies to identify biologically fluid-based, non-invasive molecular tests representing such selective panels of discerning biomarkers. One such a technology is the coupling of selective affinity-capture techniques with analytical separation techniques, as has been demonstrated with immunoaffinity capillary electrophoresis (IACE). In the IACE technology, the analyte concentrator-microreactor (ACM) device, a key component of an IACE instrument, can be used with a wide range of materials and chemistries to immobilized affinity capture substances of interest. In turn, the immobilized affinity ligands can selectively or non-selectively trap and isolate a single material or substance, or a panel of materials or substances (e.g., biomarkers), as a whole or parts, which can identify one or more diseases. The advantage of merging strategies for immunoassays and capillary electrophoresis is that now the two technologies complement the strengths of each other and work as one efficient technology. Furthermore, the technology of solid-phase capture and affinity purification have a wide variety of applications in research, clinical, pharmaceutical, forensic, environmental, food and beverage, various industrial areas, military and law enforcement institutions, terrorism (chemical or biological weapons), counterfeiting, and cultural heritage (authenticity of art work) laboratories.

Micro-scale miniaturization, represented by the IACE technology that uses a wide range of immobilized affinity ligand groups, brings major benefits to the enrichment of analytes found at low concentrations in simple and complex biological matrices. Furthermore, due to its high-resolution two-dimensionality platform, IACE has the capability of separating and quantifying intact substances and their respective modified counterparts, degradation products and/or metabolites.

The entire composition of the human body is very complex. It is not known precisely how many molecular and structural entities are, but it is known that they are many types of cellular, chemical and biochemical components, as a whole or parts and/or complexes from them, having different compositions, functions, sizes, shapes and also they vary by individual. Furthermore, the range of concentration of molecules in biological systems spans many orders of magnitude. Therefore, the use of miniaturized instrumentations and devices in the discovery of biomarkers has been a challenge for scientists. In particular, when the volumes to be used are small (e.g., microliters, nanoliters) and when the biomarkers to be analyzed are found in sub-nanomolar concentrations.

Capillary electrophoresis (CE) technology, in the conventional format and in the microchip format, has become a powerful tool employed in many laboratories in the search of important biomarker of diseases. However, the major deficiency of the CE technology for the isolation and quantification of biomarkers of interest is the limits of detection (LOD), which are constrained by the small dimension of the capillary and its reduced pathlength that hinders conventional optical detection methods such as ultraviolet detection. The steps of analyte purification and concentration for constituents present primarily in complex matrices still remains a bottleneck in the process of sample preparation.

Sample preparation is widely accepted as the most labor-intensive and error-prone part of the bioanalytical process. Sample preparation has been identified as being a bottleneck in total analysis samples, where complex matrices are used. It has become necessary then to develop sample preparation techniques to a new improved level. An integral, multi-task analyte concentrator-microreactor (ACM) device can be used for miniaturization and integration of sample preparation on-line when coupled to analytical separation instrumentation, in order to reduce laboratory workload and increase analytical performance. Furthermore, the ACM device is suitable for use with most existing applications by scaling the reagent and sample volumes, which can range from sub-microliter volumes to several milliliters.

Analyte concentrator-microreactor (ACM) devices have been developed for selective and non-selective molecular consolidations. These analyte concentrator-microreactor (ACM) devices, which are used on-line with a capillary tube or capillary channel, have been described in U.S. Pat. Nos. 5,202,010; 6,406,604; 7,329,388; 7,736,480; 7,811,436; 8,007,724; 8,007,725; 8,030,092; 8,182,746; 8,268,247; and 8,703,061 which are incorporated by references in this disclosure. U.S. Pat. No. 5,741,639 discloses the use of molecular recognition elements. U.S. Pat. No. 5,800,692 discloses the use of a pre-separation membrane for concentrating a sample. U.S. Pat. No. 7,407,568 discloses the use of sol-gel coating for on-line preconcentration in capillary electrophoresis. U.S. Pat. No. 7,828,948 discloses the use of preconcentration and separation of analytes in microchannels. U.S. Pat. No. 7,959,861 discloses the use of integrated affinity microcolumns and affinity capillary electrophoresis.

OBJECTS OF THE INVENTION

Accordingly, it is a general object of the present invention to provide an improved analyte concentrator-microreactor system, containing one or more immobilized affinity ligand groups, to be an integrated component of a capillary electrophoresis apparatus, having at least a modular, portable and interchangeable analyte concentrator-microreactor (ACM) device to perform on-line preconcentration of one or more analytes of interest, and to perform on-line chemical and/or biochemical microreactions, including chemical and biochemical synthesis, mounted to a cartridge-cassette unit to form an integrated and multi-task purpose device for capture, isolation, concentration, separation, detection, quantification and identification of one or more analytes of interest.

It is another object of the present invention that the analyte concentrator-microreactor (ACM) device is connected to one transport capillary or passage with one inlet end and one outlet end to introduce samples and buffers, and one separation capillary with one inlet and outlet ends to separate analytes of interest and/or their respective modified and/or altered corresponding counterpart.

An additional object of the present invention is to provide a user-friendly on-line sample preparation system that can be easily mounted onto a cartridge-cassette of a capillary electrophoresis apparatus, or a similar cartridge-cassette or support system of any other analytical separation instrument, in order to be readily interchangeable when positioned and connected to a separation capillary or channel to form a continue single sealed separation system.

It is a yet another object of the present invention that the inlet and outlet ends of the separation capillary or passage area of the analyte concentrator-microreactor (ACM) device can be connected to a micro-valve and a coupler or connector to the corresponding inlet and outlet ends of the separation capillary localized in the cartridge-cassette or support system forming part of a capillary electrophoresis apparatus or another type of commercial or laboratory-made analytical separation instrument. The connection of the analyte concentrator-microreactor (ACM) device corresponding to the micro-valve and coupler, of the separation capillary area, should be completely sealed to avoid any leakage of any kind.

An additional object of the present invention is that the inlet and outlet ends of the transport capillary or passage area of the analyte concentrator-microreactor (ACM) device can be connected to a micro-valve and a coupler or connector to the corresponding inlet and outlet ends of an extension capillary or passage where sample and buffers can be introduced. The connection of the analyte concentrator-microreactor (ACM) device corresponding to the micro-valve and coupler, of the transport capillary area, should be completely sealed to avoid any leakage of any kind.

It is a further object of the present invention to use the analyte concentrator-microreactor (ACM) device as a concentrator device to perform on-line binding, capture and concentration of analytes of interest present in simple and complex matrices, and as a microreactor device to perform on-line microreactions where larger polymeric macromolecules are converted into smaller molecular constituents, e.g., cleavage of a protein by an immobilized proteolytic enzyme to generate peptides, or cleavage of a larger polymeric nucleic acid by an immobilized nuclease to generate smaller nucleic acid units, or cleavage of a larger polymeric carbohydrate by an immobilized glycosidase to generate smaller sugar units, or cleavage of a complex lipid material by an immobilized lipase to generate smaller lipid units, or cleavage of larger biochemical complexes by a mixture of immobilized digestive enzymes to generate smaller corresponding constituents.

An additional object of the present invention is to provide an integrated modular and interchangeable analyte concentrator-microreactor (ACM) device of encapsulating cells and/or subcellular components to perform metabolism studies and/or cellular receptors to perform bioactivity studies.

Another object of the present invention is to provide an integrated modular and interchangeable analyte concentrator-microreactor (ACM) device capable of capture cellular, viral and/or vesicular materials or structures, as well as volatile, semi-volatile, and/or non-volatile organic and inorganic compounds from exhaled breath with the help of a tubing and an adaptor bridging and positioning the ACM device, respectively, to the mouth of a breath provider, or released volatile, semi-volatile, and non-volatile organic and inorganic compounds emitted by or extracted from plants, flowers, allergens, food, or other materials with the help of a tubing and an adaptor bridging and repositioning the ACM device, respectively, to the emitting source of emanation or emission of compounds that may be of relevance to the fragrance and flavor industries, textile and/or coloring industries, and environmental pollution agencies, and of compounds derived from skin emanations.

It is an additional object of the present invention to provide an integrated modular and interchangeable analyte concentrator-microreactor (ACM) device capable of capture of cellular, viral and/or vesicular materials, as well as volatile, semi-volatile, and/or non-volatile organic and inorganic compounds from nasal or nasopharyngeal aspirate fluid, and from nipple aspirate fluid with the help of a tubing and a modified adaptor bridging and positioning the ACM device, respectively, to the nose of a nasal or nasopharyngeal fluid provider, or to the nipple of a breast fluid provider.

It is a further object of the present invention that the analyte concentrator-microreactor (ACM) device is surrounded by micro-valves to create a controllable microenvironment (e.g., time of reaction, temperature, mixing of reagents) to perform on-line optimal concentrations or to carry out on-line optimal microreactions.

It is a another object of the present invention to connect the modular, portable, interchangeable, and integral analyte concentrator-microreactor (ACM) device, with a transport capillary or passage and a separation capillary or passage, directly to a detector, such as a mass spectrometer, without the need for a connection to a capillary electrophoresis apparatus or another analytical separation instrument.

It is a yet another object of the present invention to provide a modular and interchangeable analyte concentrator-microreactor (ACM) device which may be easily and efficiently manufactured and marketed.

An additional object of the present invention is to provide a modular and interchangeable analyte concentrator-microreactor (ACM) device that can be mounted and incorporated as a functional and integrated component of an existing or custom-made cartridge-cassette utilized in laboratory-made or commercial analytical separation instruments.

Another object of the present invention is to provide a modular and interchangeable analyte concentrator-microreactor (ACM) device having a separation inlet port and a separation outlet port connected respectively to the inlet end and the outlet end of the separation capillary or passage, and having a transport inlet port and a transport outlet port connected respectively to the inlet end and the outlet end of the transport capillary or passage, the transport inlet port and the transport outlet port positioned in a parallel configuration to each other.

SUMMARY OF THE INVENTION

The present invention provides a modular, portable, and interchangeable analyte concentrator-microreactor (ACM) device, containing one or more immobilized affinity ligand groups, surrounded with four micro-valves, to become an integrated system when mounted to a cartridge-cassette or a similar support containing a separation capillary or column that is part of a capillary electrophoresis apparatus or any other kind of an analytical separation instrument. The integrated system permits analyte concentration and/or microreactions to be carried out followed by the separation of the analytes of interest and/or their respective modified and/or altered corresponding counterpart. In one aspect of the invention, a sample containing one or more analytes of interest and/or their respective modified and/or altered corresponding counterpart is passed through an analyte concentrator-microreactor (ACM) device localized at the intersection point and connected to a transport capillary and to a separation capillary or channel. Furthermore, at or near the inlet and outlet ports of the transport and separation capillary or channel there are positioned four micro-valves, one at each port location, capable of controlling the flow of fluid. The integrated system becomes a closed interconnected system that is completely sealed to avoid any leakage of any kind.

In general, the integrated, multi-task analyte concentrator-microreactor (ACM) device can be used for performing on-line a single or a plurality of affinity capturing and enzymatic methods, including synthesis of small molecules and biomolecules. The affinity capturing methods typically bind and retain a wide range of chemical and biochemical substances, cells, subcellular structures, cellular organelles or components, cell-derived vesicles, globules and other particle materials, such as viruses, prions, spores and microorganisms, as a whole or parts and/or complex of them. Affinity ligands and/or enzymes are usually immobilized to surfaces of the inner wall of the analyte concentrator-microreactor (ACM) device, or immobilized to micro- or nano-particles or structures contained within the inner cavity or channel of the analyte concentrator-microreactor (ACM) device.

Immunoaffinity capillary electrophoresis (IACE) technology offers several advantages over traditional immunoassays and conventional capillary electrophoresis, and even nano-HPLC. Conventional capillary electrophoresis and nano-HPLC can achieve improved separation selectivity and short analysis time, when compared to other separation techniques. Immunoassays can also be advantageous when referred to obtain high-sensitivity levels and high-throughput in the quantification of a wide range of analytes. However, each of these technologies has several disadvantages as well. The combination of the two immuno-separation principles which make each technology unique has created a powerful two-dimensional technology, that when coupled to an appropriate detector produces a highly-selective on-line preconcentration and a high-resolution separation capability, for the capture, isolation, purification, concentration, separation, detection, quantification, and characterization of a wide range of small molecules, biomolecules, cells and subcellular structures, as a whole or parts and/or complex of them. Another important function of the integrated analyte concentrator-microreactor (ACM) device of the present invention is to perform as a microreactor, where chemical and biochemical reactions can occur, including synthesis of chemical and biochemical molecules, and metabolic studies in a micro-controlled environment. Cellular receptors and/or membranes can be contained within the internal cavity or channel of the ACM device to perform metabolic studies or bioassays. Furthermore, the integrated analyte concentrator-microreactor (ACM) device of the present invention can be coupled to powerful detectors, including, for example, a laser-induced fluorescence detector to enhance sensitivity, and to a mass spectrometer, to provide detailed molecular information of the analytes of interest.

A major characteristic of the design of the analyte concentrator-microreactor (ACM) device of the present invention is to allow sample and washing buffer introduction in a direction perpendicular to the separation capillary, in order to preserve the integrity of the separation capillary or passage. In addition, the inlet port and the outlet port of the transport capillary or channel are positioned in a parallel arrangement to facilitate the introduction of sample and buffers when mounted onto the cartridge-cassette and incorporated into a capillary electrophoresis apparatus or any other kind of analytical separation instrument.

The analyte concentrator-microreactor (ACM) device of the present invention is specifically based on the technology of immunoaffinity capillary electrophoresis (IACE) and contains selective and immobilized directly to the surface of the inner wall of the main cavity or channel, or to surfaces of beads, polymers, or macro-nano-structures positioned within the main cavity or channel of the analyte concentrator-microreactor (ACM) device. The analyte concentrator-microreactor (ACM) device of the present invention can also contain non-selective affinity ligand groups immobilized directly to the surface of the inner wall of the main cavity or channel, or to surfaces of beads, polymers, or macro-nano-structures positioned within the main cavity or channel of the analyte concentrator-microreactor (ACM) device. Although there are several non-selective affinity ligand groups that can be used to capture certain types of analytes, in general, highly selective, specific and geometrically defined combinations of several interactions are used to obtain very high specificities of binding to obtain the selective capture of an analyte of interest. The immobilized affinity ligand groups facilitate the isolation, enrichment and purification of the analytes of interest. Furthermore, when connected to a separation capillary or channel and an appropriate detector, it will separate, quantify and identify a wide range of small molecules, biomolecules, cells and subcellular structures, as a whole or parts, or complex of them, present primarily at low- and medium abundance in simple and complex chemical and biological mixtures or matrices. In addition, the technology can be applied to the determination of analytes present at high concentrations and at different molecular organizations or structures simultaneously with other chemical and biological entities, including bacteria, yeasts, viruses and prions.

Although analytes of interest are aimed to be bound, selectively or non-selectively, to one or more affinity ligands immobilized to the surface of beads, matrices, or directly to the inner surface of the cavity or channel comprising the capturing or reaction area of the analyte concentrator-microreactor (ACM) device, some degree of binding of unwanted materials usually occurs. Such non-specific binding of unwanted materials may occur primarily within the capturing or reaction area of the ACM device and/or to the walls of the transport capillary or passage. Such unwanted non-specifically bound compounds and/or materials can be removed by a cleaning buffer or solutions containing detergents and/or other additives. The purified and concentrated bound analytes of interest can then be released onto the separation capillary or channel by a plug of an appropriate elution buffer or solution for further separation of the main analytes of interest and/or their respective modified and/or altered corresponding counterparts.

There are many advantages of introducing the sample in an orthogonal arrangement (e.g., cruciform, staggered, or parallel) with respect to the separation capillary or channel. Of special interest is the fact that the full range of chemical or biological concentrations that are needed to be detected in biological specimens spans many orders of magnitude (at least 20 orders of magnitude). Therefore, the analyte concentrator-microreactor (ACM) device, designed as a miniaturized component, for the capturing and isolation of the full range of potential analytes of interest, it is capable of processing large as well as small sample volumes. The variable length of the inner cavity or channel of the analyte concentrator-microreactor (ACM) device allows the immobilization of one or several immobilized affinity ligand groups or receptors capable of capturing and isolating analytes found at different concentrations. Furthermore, since the affinity ligands or receptors can be immobilized directly to the surface of the wall of the inner cavity or channel of the analyte concentrator-microreactor (ACM) device, it is possible to capture a single cell, cell-derived organelle, or cell component (e.g., blood cells, cancer cells, mitochondria, vesicle, bacteria, yeast, virus, prion, other microorganisms, etc.) present in small or large volumes of biological fluid. Moreover, the analyte concentrator-microreactor (ACM) device is part of an integral unit that include a transport capillary or channel, micro-valves, and a separation capillary or channel coupled to one or more powerful detectors, then it is possible to separate, detect and identify all kinds of substances, particles, structures, and/or materials present at a wide range of units or concentrations in simple or complex matrices, at sub-microliter and milliliter volume quantities.

Unlike conventional solid-phase extraction (SPE) techniques, the immobilized affinity ligands are integrated into the ACM device, that allows for low void volume sample manipulations either manually or in combination with laboratory robotics using electronic-controlled circuitry, and/or a smartphone-adapted controlling system. The key aspect of the use of the miniaturized ACM device is that the solvent volume used for the elution of the bound analytes is in the order of low nanoliter volumes. This miniaturized technique is very promising because it is fast, simple and it requires very small volume of samples to produce comparable results to conventional SPE techniques; it is environmental friendly using minimum quantities of organic solvents, it is cost-effective, and can be used as a portable unit in remote locations. In addition, the integrated, multi-task ACM device coupled to capillary electrophoresis and powerful detectors, such as a laser-induced fluorescence detector and/or a mass spectrometer, is of great importance in the capture, isolation, purification, concentration, release, separation, detection, quantification, and identification of biomarkers of relevance to clinical, forensic toxicology, environmental analysis areas, and many other applications.

The invention will be more fully described by reference to the following drawings.

DETAILED DESCRIPTION OF THE INVENTION

Figure 1:
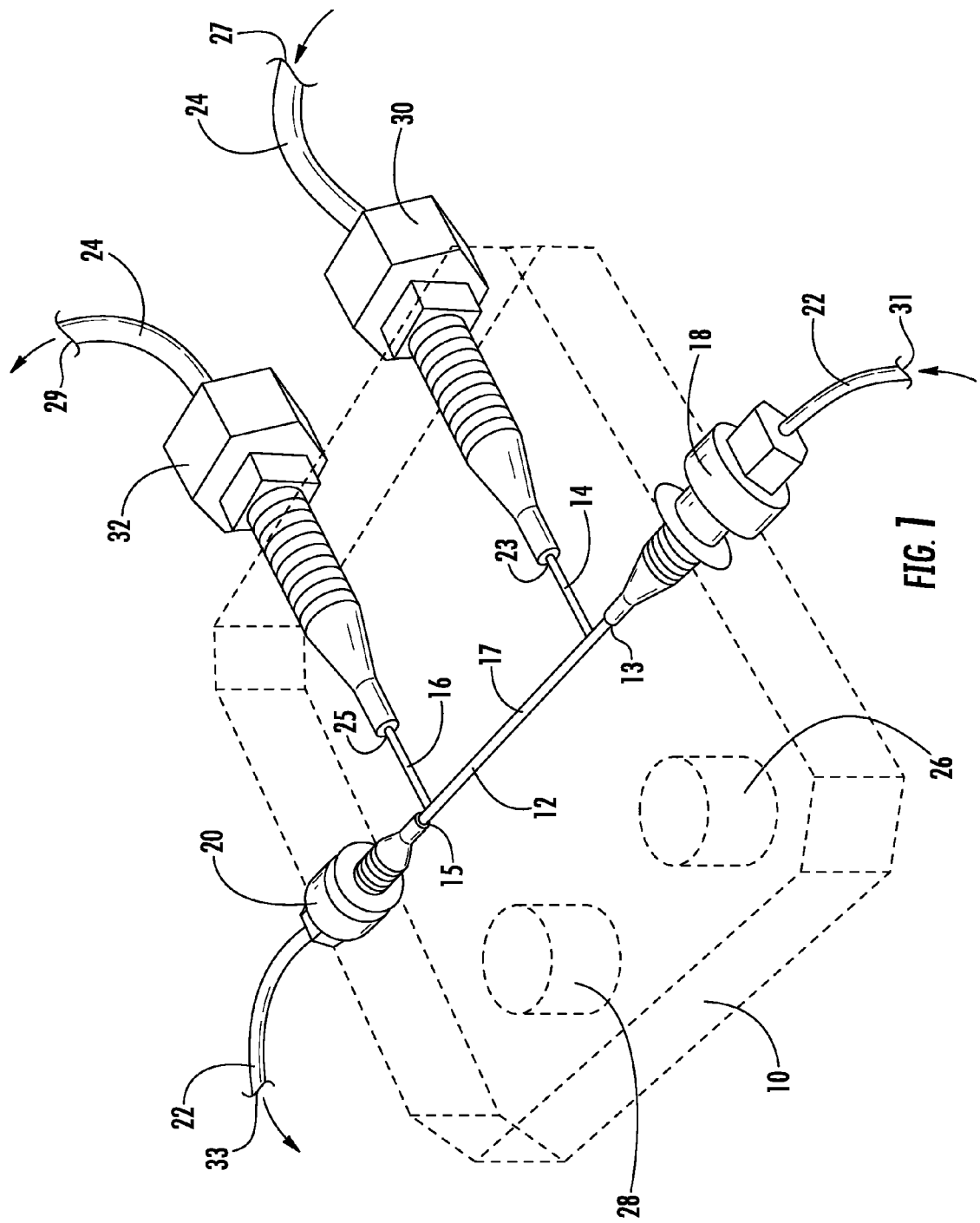
FIG. 1 illustrates a single analyte concentrator-microreactor (ACM) device having four entrance-exit ports identified as connection areas. Two are connecting areas to the analyte concentrator-microreactor (ACM) device with the transport capillary; and two are connecting areas to the analyte concentrator-microreactor (ACM) device with the separation capillary. The connecting areas to the analyte concentrator-microreactor (ACM) with the transport capillary are in a parallel arrangement. The arrows positioned at the transport capillary location represent the direction of sample and buffers introduction. The arrows positioned at the separation capillary location represent the direction of buffers introduction and the direction of separation of the analytes bound to and released from the analyte concentrator-microreactor (ACM) device.

Reference will now be made in greater detail to a preferred embodiment of the invention, an example of which is illustrated in the accompanying drawings. Wherever possible, the same reference numerals will be used throughout the drawings and the description to refer to the same or like parts.

FIG. 1 illustrates modular, portable and interchangeable analyte concentrator-microreactor (ACM) device 10 of the present invention, containing one or more immobilized affinity ligand groups, that can be mounted directly onto a cartridge-cassette unit of a capillary electrophoresis apparatus, or a similar cartridge-cassette or support unit of a gas-chromatography apparatus, a liquid-chromatography apparatus, another analytical separation apparatus, including microfluidic devices, or to a combined apparatus containing functional features of all analytical separation instrumentation. Apertures 26 and 28 in analyte concentrator-microreactor (ACM) device 10 can be used for mounting of analyte concentrator-microreactor (ACM) device 10 through poles or support members (not shown) received in apertures 26 and 28. Analyte concentrator-microreactor (ACM) device 10 includes inner cavity or channel 12 forming an internal area or channel. Two connecting cavities or channels 14 and 16 that form part of the transport capillary or passage are connected parallel to one another to inner cavity or channel 12. Inner cavity or channel 12 is an area that can hold bead structures or micro-nano-materials to which affinity ligands can be immobilized to their surfaces. Similarly, the affinity ligands can be immobilized directly to the surface of the wall 17 of inner cavity or channel 12. Inner cavity or channel 12 is the actual concentrator-microreactor area, where capture, isolation, concentration and release of analytes of interest, and/or their respective modified and or altered corresponding counterpart, occur. Inner cavity or channel 12 is also the area where chemical and/or biochemical reactions occur. Inner cavity 12 is also the area the provides a place of shelter for encapsulated cellular and/or subcellular structures and/or cellular receptors, where metabolic studies and/or bioactivity studies can be carried out. The arrows next to the inlet 31 and outlet 33 areas of the separation capillary connected to analyte concentrator-microreactor (ACM) device 10 indicate the direction of the buffers introduction and the direction of the separation of the bound and released analytes.

Couplers 18 and 20 connect separation capillary or passage 22 to inner cavity or channel 12 to form a continued single separation capillary. Couplers 18 and 20 are manufactured to precision to make the separation capillary and transport capillary connection a completely closed and sealed system. All connecting parts of integrated ACM device 10 must be tightly connected, avoiding any possibilities of leakages of fluid exit and of air penetration to the system. Coupler 18 connects separation capillary or passage 22 through inlet port 13 of inner cavity or channel 12, and coupler 20 connects separation capillary or passage 22 through outlet port 15 of inner cavity or channel 12.

Couplers 30 and 32 connect transport capillary or passage 24 to inner cavity or channel 12 through cavities or channels 14 and 16. Coupler 30 is located at inlet port 23, where the sample and buffers enter into analyte concentrator-microreactor (ACM) device 10, as indicated by the arrow next to the entrance location 27 of transport capillary or passage 24. Coupler 32 is located at outlet port 25, where the sample and buffers, to clean and condition the system, exit from analyte concentrator-microreactor (ACM) device 10, as indicated by the arrow next to the exit location 29 of transport capillary or passage 24.

Affinity ligand groups can be immobilized to a wide range of material surfaces by one or more chemical modification techniques, including covalent and non-covalent methods, and also including self-assembled monolayers that produce surfaces with well-defined compositions on substrates. The immobilization of affinity ligand groups to micro-nano structures, and positioning of the micro-nano structures within inner cavity or channel 12 of analyte concentrator-microreactor (ACM) device 10, or directly to the surface of wall 17 within inner cavity or channel 12 of analyte concentrator-microreactor (ACM) device 10, has been described in U.S. Pat. Nos. 7,329,388; 7,736,480; 7,811,436; 8,007,724; 8,007,725; 8,030,092; 8,182,746; 8,268,247; and 8,703,061 hereby incorporated by reference in their entireties into this application, or to a matrix-like assembly held within inner cavity or channel 12 of the type described in U.S. Pat. No. 5,202,010, hereby incorporated by reference in its entirety into this application. The collective mass of the matrix can be provided in many forms by large quantities of chemically and mechanically stable micro-nanostructures such as beads, chips, fibers, filaments, monolithic polymers, sol-gel or the like. Individual substrates can be made from glass, plastic, or polymeric materials, ceramic, or metallic compositions, and mixtures thereof. Interconnected beaded or polymerized micro-nanostructures can form a net or scaffold that can be sustained by itself without the need of a frit structure, a semi-permeable membrane, or a constricted area. All other free-floating micro-nanostructures may need a frit structure, a semi-permeable membrane, a constricted area to retain the free-floating micro-nanostructures, a diameter of inner cavity or channel 12 to retain the free-floating micro-nanostructures being larger than a diameter of separation capillary or passage 22, or a magnet if the micro-nanostructures contain metal chemical groups or metallic materials and a magnet associate with inner cavity or channel 12, to be retained within inner cavity or channel 12 of analyte concentrator-microreactor (ACM) device 10.

Covalently or non-covalently affinity ligand groups coated or immobilized onto the surfaces of the beaded micro-nano-structures, monolithic polymers or sol-gel positioned within inner cavity or channel 12 of analyte concentrator-microreactor (ACM) device 10, or directly onto the surface or wall 17 of inner cavity or channel 12 of analyte concentrator-microreactor (ACM) device 10, are analyte specific antibodies or other type of affinity ligand groups which are suitable to capture selectively one or more analytes of interest and/or their respective modified and/or altered corresponding counterpart. Non-selective affinity ligand groups can also be immobilized to the surface of the microstructures positioned within inner cavity or channel 12 of analyte concentrator-microreactor (ACM) device 10, or directly onto the surface or wall 17 of inner cavity or channel 12 of analyte concentrator-microreactor (ACM) device 10, to capture usually a group of substances with certain physico-chemical properties. In the case of binding to biological receptors, selective ligand groups have a tendency to bind to a very limited types of receptors (usually the binding is more specific), whereas non-selective ligand groups bind to several types of receptors (usually the binding is less specific). Binding selectivity refers to the differing affinities with which different ligands bind to a substrate forming a complex. The concept of selectivity is used to quantify the extent to which a given substrate, A, binds two different ligands, B and C. Affinities can be classified as having ligand group(s) with high affinity binding capability or with low affinity binding capability. In general, high-affinity ligand binding results from greater intermolecular force between the ligand and its receptor while low-affinity ligand binding involves less intermolecular force between the ligand and its receptor. In general, high-affinity binding involves a longer residence time for the ligand at its receptor binding site than is the case for low-affinity binding.

The affinity ligands immobilized to the surface of the micro-nano-structures, or the matrix assembly, or the surface of inner wall 17 of inner cavity or channel 12 forming the analyte concentrator-microreactor area of analyte concentrator-microreactor (ACM) device 10 can include biological and non-biological ligand groups, such as intact polyclonal or monoclonal antibodies, single-chain antibodies, antibody fragments, antibody-drug conjugates, organic and inorganic compounds, antigens, protein A, protein G, protein A/G, protein L, lectins, enzymes, cofactors, coenzymes, drugs, toxins, vitamins, hormones, proteins, peptides, polymeric nucleotides such as DNA and RNA, oligonucleotides, polymeric carbohydrates such as glycogen and cellulose, monomeric sugars, simple and complex lipids, monomeric constituents of lipids, complexes of these molecules such as glycoproteins and glycolipids, aptamers, viruses, cells, subcellular structures, cellular organelles or components, cell-derived vesicles, globules, prions, receptors, membranes, vesicules, dyes, ions, ligands with metal-containing moieties, ligands with organometallic-containing moities, ligands with hydrophobic-containing moieties, ligands with hydrophilic-containing moieties, ligands with mixed-mode-containing moieties, alumina, activated charcoal, recombinant ligands, synthetic ligand or the like. The analytes of interest and/or their respective modified and/or their altered corresponding counterpart, as a whole or parts, or complexes of them, include biological and non-biological compounds, such as intact polyclonal or monoclonal antibodies, single-chain antibodies, antibody fragments, antibody-drug conjugates, organic and inorganic compounds, antigens, protein A, protein G, protein A/G, protein L, lectins, enzymes, cofactors, coenzymes, drugs, toxins, vitamins, hormones, proteins, peptides, polymeric nucleotides such as DNA and RNA, oligonucleotides, polymeric carbohydrates such as glycogen and cellulose, monomeric sugars, simple and complex lipids, monomeric constituents of lipids, complexes of these molecules such as glycoproteins and glycolipids, aptamers, viruses, cells, subcellular structures, cellular organelles or components, cell-derived vesicles, globules, prions, receptors, membranes, vesicules, dyes, ions, metal-containing moieties, organometallic moities, recombinant ligands, synthetic ligand or the like.

Immobilized affinity ligand groups, such as antibodies and enzymes, to a solid support can become more stable than when are in solution, and can be employed multi-times for extended period of time without loss of activity.

In order to provide a microenvironment with optimal conditions for the interaction between the immobilized affinity ligands, the analytes of interest and/or their respective modified and/or altered corresponding counterpart, as a whole or parts, or as complexes from them, as well as reactants and other reagents, it is used a micromixing system, a microwave pulsing system, and/or a temperature controlled system. The accessories can be annexed to the analyte concentrator-microreactor (ACM) device (FIG. not shown).

The analytes of interest can be chemical and/or biochemical in nature and they can be present in simple and complex matrices. Some of the biological matrices or specimens containing fluids, structures and/or globules are intracellular fluids, extracellular fluids, blood, serum, plasma, lymphatic fluid, breast milk, amniotic fluid, pericardial fluid, peritoneal fluid, gastric fluid, aqueous and vitreous humour, exudates, pus, urine, saliva, sputum, mucus, semen, vaginal and cervico-vaginal secretion, serumen (earwax), sebum (skin oil), chyle, chyme, cerebro-spinal fluid, bile, sweat, tears, meconium, exhaled breath, nasal secretion and lavage, nasal aspirate fluid, broncoalveolar fluid, nasopharyngeal secretions, airway secretions, nasal wash, nipple aspirate fluid, other lavage fluids, hair, nail, stool (feces), vomit, extracts of tissues or cells, intact normal or pathogenic cells, including circulating tumor cells, cell parts, cellular organelles or components, cell-derived vesicles, globules, microorganisms, yeast, fungus, archaea, viruses, prions and parasites, or a combination thereof.

In addition to perform as an on-line concentrator, analyte concentrator-microreactor (ACM) device 10, can perform as a microreactor, where chemical and biochemical reactions can occur, including synthesis of chemical and biochemical molecules, and metabolic studies in a micro-controlled environment. Cellular receptors and/or membranes can be contained within the internal cavity or channel of the ACM device to perform metabolic studies or bioassays.

The portable and interchangeable analyte concentrator-microreactor (ACM) device 10 can be color-coded to represent the presence of specific affinity ligands and/or a particular functionality. For example, it can be used for the determination of a certain number of analyte biomarkers associated to the diagnosis and/or prognosis of a particular disease or toxic state, and/or to identify the normality-abnormality of a certain organ, tissue cluster cells, or circulating cells.

Figure 2:
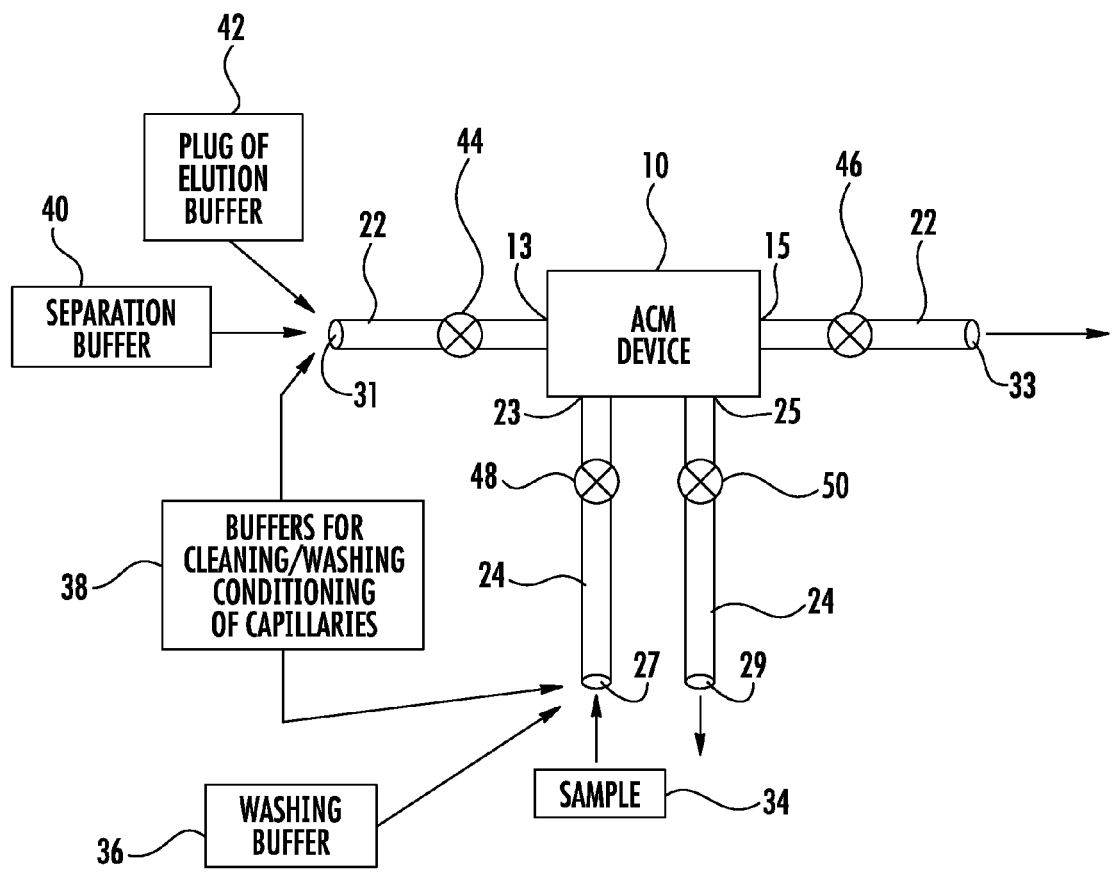
FIG. 2 is a schematic representation of the sequence of events describing (a) the cleaning and conditioning of the transport and separation capillary having inlet and outlet ends, and the inner cavity or channel of the analyte concentrator-microreactor (ACM) device, prior to sample introduction; (b) the washing of the transport and separation capillary, and the inner cavity or channel of the analyte concentrator-microreactor (ACM) device after sample introduction followed by the introduction of an optimal separation buffer; (c) the process of elution or release of the one or more analytes of interest and/or their respective modified and/or altered corresponding counterpart bound to the analyte concentrator-microreactor (ACM) device by a plug of an elution buffer or solution; and (d) the separation of the released analytes of interest into the separation capillary by one or more of any of the modes capillary electrophoresis using an optimal buffer or solution. The arrows positioned at the transport capillary location represent the direction of sample and buffers introduction. The arrows positioned at the separation capillary location represent the direction of buffers introduction and the direction of separation of the analytes bound to and released from the analyte concentrator-microreactor (ACM) device.

FIG. 2 illustrates the sequence of events required to perform solid-phase extraction using immunoaffinity capillary electrophoresis for the capture, isolation, purification and concentration of a wide range of analytes, including small molecular weight substances, polymeric biomolecules, metabolic compounds, cellular and subcellular structures, cellular organelles or components, cell-derived vesicles, globules, viruses, prions, and other particles, vesicular or globular materials, as a whole or parts, or complexes of them, or the like. When separation capillary 22 connected to analyte concentrator-microreactor (ACM) device 10, containing immobilized affinity ligands, is coupled to the main separation capillary or passage contained within a cartridge-cassette of a laboratory-made or commercial capillary electrophoresis, or to a similar cartridge-cassette support unit of any other analytical separation instrument, such as nano-HPLC or gas chromatography, a powerful tool is generated for affinity capture, isolation, purification, separation, detection, quantification and characterization of a wide range of molecules present in simple and complex mixtures and found at low, intermediate, or high concentrations.

Analyte concentrator-microreactor (ACM) device 10 has inlet port 13 and outlet port 15 connected to inner cavity or channel 12 of the device, which serve as the connection points for separation capillary or passage 22, through couplers 18 and 20 (depicted in FIG. 1). Similarly, analyte concentrator-microreactor (ACM) device 10 has inlet port 23 and outlet port 25 connected to inner cavity or channel 12 of the device, which serve as the connection points for transport capillary or passage 24, through couplers 30 and 32 (depicted in FIG. 1). Analyte concentrator-microreactor (ACM) device 10 is surrounded by four micro-valves 44, 46, 48, and 50. Micro-valve 44 is connected to separation capillary or passage 22 near inlet port 13 of analyte concentrator-microreactor (ACM) device 10; micro-valve 46 is connected to separation capillary or passage 22 near outlet port 15 of analyte concentrator-microreactor (ACM) device 10; micro-valve 48 is connected to transport capillary or passage 24 near inlet port 23 of analyte concentrator-microreactor (ACM) device 10; and micro-valve 50 is connected to transport capillary or passage 24 near outlet port 25 of analyte concentrator-microreactor (ACM) device 10. Inlet end 27 and outlet end 29 of transport capillary or passage 24 are positioned in a parallel configuration to each other when connected to inner cavity or channel 12 of analyte concentrator-microreactor (ACM) device 10 through connecting cavities or channels 14 and 16, as shown in FIG. 1.

Referring to FIG. 2, before sample 34 is introduced through inlet end 27 of transport capillary or passage 24, a few steps are carried out to clean and condition the system. When analyte concentrator-microreactor (ACM) device 10, containing the immobilized affinity ligand groups to micro-nano-structures or directly onto the inner wall, is mounted and secured onto the cartridge-cassette, an integral system is formed once it is connected to separation capillary or passage 22, transport capillary or passage 24, micro-valves 44, 46, 48, and 50, and their respective couplers or connectors 18, 20, 30, and 32 (depicted in FIG. 1). In an additional embodiment shown in FIG. 3 connectors 52, 54, 56 and 58 can be used to facilitate the connection to separation capillary or passage 22 and to transport capillary or passage 24, to produce an easy interchangeable ACM device system.

Referring to FIG. 2 during operation, cleaning, washing, and conditioning buffers and/or solutions 38 are introduced separately, independently and in sequential order through separation capillary or passage 22 from inlet end 31 to outlet end 33 when micro-valves 44 and 46 are opened and micro-valves 48 and 50 are closed. The next step is to introduce separately, independently and in sequential order cleaning, washing, and conditioning buffers and/or solutions 38 through transport capillary or passage 24 from inlet end 27 to outlet end 29 when micro-valves 48 and 50 are opened, and valves 44 and 46 are closed. The final step is to add an appropriate separation buffer 40 to separation capillary or passage 22 from inlet end 31 to outlet end 33. The arrows positioned at the transport capillary location represent the direction of sample and buffers introduction. The arrows positioned at the separation capillary location represent the direction of buffers introduction and the direction of separation of the analytes bound to and released from the analyte concentrator-microreactor (ACM) device.

After the complete integral ACM device system is cleaned, conditioned, and equilibrated with separation buffer 40, it is ready to function. Sample 34 is introduced from inlet end 27 of transport capillary or passage 24, through analyte concentrator-microreactor (ACM) device 10, all the way through transport capillary or passage 24 to a waste container (not shown) localized at the exit area of outlet end 29 of transport capillary or passage 24, while maintaining micro-valves 48 and 50 opened, and valves 44 and 46 closed. This step is preferred to be carried out under controlled microenvironmental conditions to optimize binding of the analytes of interest to the affinity ligand groups immobilized within analyte concentrator-microreactor (ACM) device 10, such as temperature, time of reaction, and mixing of reactants. After sample introduction, a washing procedure is followed by the introduction of washing buffer 36 and while maintaining micro-valves 48 and 50 opened, and valves 44 and 46 closed. The addition of the washing buffer 36, introduced into transport capillary or passage 24, is necessary to eliminate all excess amount of sample and any quantity of unwanted substances bound non-specifically to certain areas of the inner surface of transport capillary or passage 24 and to certain areas of the surfaces of the microstructures positioned at analyte concentrator-microreactor (ACM) device 10, or to certain areas of inner wall 17 of ACM device 10 itself. It is preferred also to add washing buffer 36 to separation capillary or passage 22, to ensure that even small amounts of unwanted materials bound to certain areas of the inlet and outlet connection points of the separation capillary or passage 22, are eliminated. At this stage a fresh separation buffer 40, typically filtered and degassed, or a separation buffer containing a liquid gel-type of constituent, is added prior to start the elution and separation procedures.

Once all analytes of interest are bound to the immobilized affinity ligand groups contained within the analyte concentrator-microreactor (ACM) device 10, a process of elution, desorption, or release of the bound substances can be performed. Disruptors of the binding between the bound analyte(s) and the affinity ligand group(s) are needed to release the bound analyte. A number of solutions having low or high pHs, containing high salt concentrations, or containing substances like urea, organic solvents, a structurally-related analog substance competing for the binding, or a combination of them, are ideal disruptors of the reversible affinity binding. Affinity bindings can be weak or strong; therefore, elution conditions may vary for different bound analytes. When using a miniaturized analyte concentrator-microreactor (ACM) device 10, the process of elution requires a small volume or plug of buffer or solution 42, usually less than about 200 nanoliters to release the bound analytes from the ACM device. Immediately after the introduction of the plug of elution buffer or solution 42 to inlet end 31 of separation capillary or passage 22, separation capillary or passage 22 is connected to separation-buffer container for separation buffer 40. When a plug of the elution buffer or solution 42 passes through the internal cavity or channel of ACM device 10, the bound analytes are released and transferred to separation capillary or channel 22. The process of separation can be carried out by applying one or more of any of the modes of capillary electrophoresis. The separation process starts when the high-voltage power supply, and/or pressure, is activated manually or electronically using controllable sets of operation and/or an electronically-controlled circuitry adapted to be operated by a personal digital assistant or a cell phone. For example, the cell phone can be a smartphone such as an IPHONE manufactured by Apple or a GALAXY manufactured by Samsung. A plug of the elution buffer or solution 42 can also contain a chromophoric substance to tag or derivatize on-line the one or more analytes as they are released from ACM device 10 into separation capillary or passage 22. The derivatized analytes usually have higher detection sensitivities than the non-derivatized counterparts. Derivatization of analytes can also be performed in the entire sample containing the analytes of interest prior to sample introduction into transport capillary or passage 24 (off-line derivatization). The process of derivatization can also be carried out as a post-separation process (still on-line derivatization) at outlet end 33 of separation capillary or passage 22, after separation of the analytes, but prior to detection. A similar or modified analyte concentrator-microreactor (ACM) device (not shown) can be installed at the outlet end of the separation capillary to carry out the process of post-separation derivatization.

All three processes of sample and buffer introduction can be carried out by electrically-driven and/or mechanically-driven pressures. Usually, the introduction of samples, buffers or solutions is carried-out by mechanically-driven pressure. Separation is usually carried out by electrophoresis principles, electro-osmotic flow, mechanical pressure, or a combination of electro-osmotic flow and mechanical pressure, depending on the type of sample to be analyzed, the constitution of the separation buffer, and some experimental conditions.

The bound, released, and separated analytes are finally detected by one or more on-line or off-line detectors, such as ultraviolet, fluorescence, laser-induced fluorescence, mass spectrometer, nuclear magnetic resonance, circular dichroism, charged coupled device (CCD), electrochemical, conductivity, radioactive, or the like. The process of separation of the released analytes can also be subjected to an optimization process; for example, the separation capillary or passage can be temperature controlled.

The use of analyte concentrator-microreactor (ACM) device 10 depicted in FIGS. 1 and 2 is configured to function as both a concentrator and as a microreactor. For example, rather than immobilizing an antibody specific for one antigen to the ACM device, it is possible to immobilize an enzyme for one specific substrate, or a family of related substances. Proteolytic enzymes can be immobilized to the microstructures or to wall contained within the cavity of the analyte concentrator-microreactor (ACM) device, to cleave proteins to generate peptides. Similarly, other larger polymeric macromolecules can be converted into smaller molecular constituents, e.g., cleavage of a larger polymeric nucleic acid by an immobilized nuclease to generate smaller nucleic acid units, or cleavage of a larger polymeric carbohydrate by an immobilized glycosidase to generate smaller sugar units, or cleavage of a larger polymeric lipid material by an immobilized lipase to generate smaller lipid units, or cleavage of larger biochemical complexes by a mixture of immobilized digestive enzymes to generate smaller corresponding constituents. An additional function of the analyte concentrator-microreactor (ACM) device is to perform chemical and biochemical synthetic reactions to be carried out within the cavity or channel of the ACM device. Example of synthetic reactions include peptide synthesis, nucleic acid synthesis, and the synthesis of other organic and inorganic materials. A further function of the analyte concentrator-microreactor (ACM) device is to perform protein sequencing, and the sequencing of other biopolymers, such as for example polynucleotides, polysaccharides, and other complex biomolecules.

Figure 3:
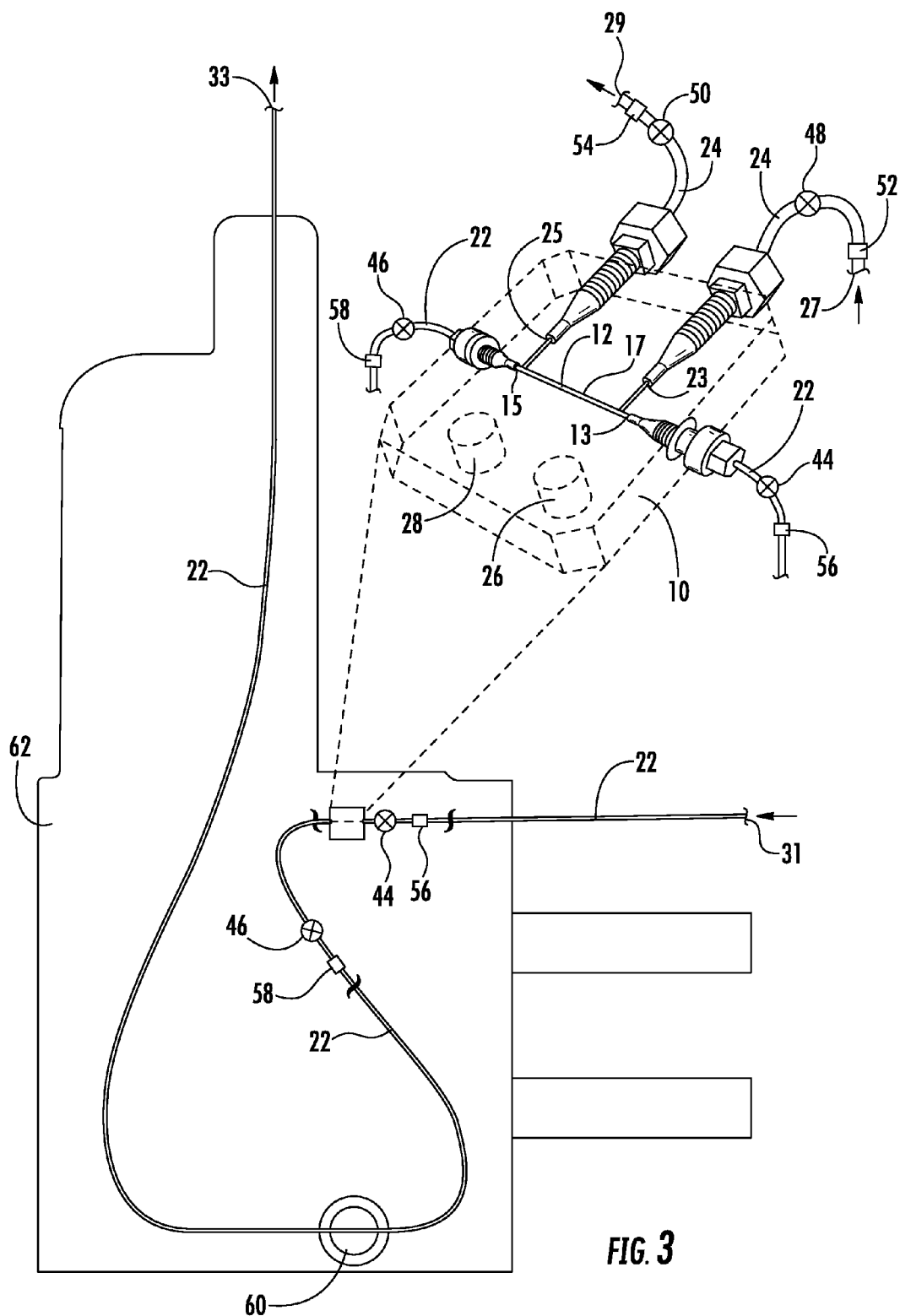
FIG. 3 is an enlarged perspective view of the analyte concentrator-microreactor (ACM) device mounted to a cartridge-cassette unit of a capillary electrophoresis apparatus or another similar unit of any other analytical separation apparatus used for the capture, isolation, concentration, release, separation, detection, quantification, and identification of simple and complex molecules, materials, or structures. Both transport capillary and separation capillary are connected to corresponding valves controlling the path of fluids. In addition, as a modular and interchangeable unit, the analyte concentrator-microreactor (ACM) device is connected through couplers from the inlet and outlet areas of the elongated inner cavity or channel of the ACM device to the corresponding inlet and outlet ends of the separation capillary positioned in the cartridge-cassette unit. The inlet and outlet areas of the parallel connection to the transport capillary may also be connected through couplers to longer extensions of their corresponding inlet and outlet ends. The arrows positioned at the ACM device location represent the direction of the path of fluid (sample and buffers) through the analyte concentrator-microreactor (ACM) device from inlet to outlet ends. The arrows positioned at the transport capillary location represent the direction of sample and buffers introduction. The arrows positioned at the separation capillary location within the cartridge-cassette unit represent the direction of buffers introduction and the direction of separation of the analytes bound to and released from the analyte concentrator-microreactor (ACM) device.

FIG. 3 illustrates a view of portable, interchangeable analyte concentrator-microreactor (ACM) device 10 mounted onto cartridge-cassette 62 support. In this particular embodiment separation capillary or passage 22 is connected to analyte concentrator-microreactor (ACM) device 10 by couplers 56 and 58 and micro-valves 44 and 46 forming a single integrated and continued separation capillary, from an inlet end 31 to an outlet end 33. Transport capillary or passage 24 is connected to analyte concentrator-microreactor (ACM) device 10 by couplers 52 and 54 and micro-valves 48 and 50 forming a single integrated and continued transport capillary from inlet end 27 to outlet end 29. The arrows positioned at the ACM device location represent the direction of the path of fluid (sample and buffers) through analyte concentrator-microreactor (ACM) device 10 from inlet end 27 to outlet end 29 of the transport capillary or passage 24. The arrows positioned at the cartridge-cassette location represent the direction of buffers introduction and the direction of separation of the analytes bound to and released from analyte concentrator-microreactor (ACM) device 10 from inlet end 31 to outlet end 33 of the separation capillary or passage 22.

The analytes bound to and released from analyte concentrator-microreactor (ACM) device 10 are separated within separation capillary or passage 22 passing through an on-line detector system 60 and continue to outlet end 33 of separation capillary or passage 22 to an off-line detector, as indicated by the arrow positioned at outlet end 33 of the separation capillary or passage 22.

The optimal performance of analyte concentrator-microreactor (ACM) device 10 is dependent on the coordination of operation of all four micro-valves 44, 46, 48, and 50, as shown in FIGS. 2 and 3. For convenience of coupling segmented separation capillary or passage 22 to analyte concentrator-microreactor (ACM) device 10, once is mounted in the cartridge-cassette or prior to be mounted, easy to operate couplers 56 and 58 are installed.

Figure 4:
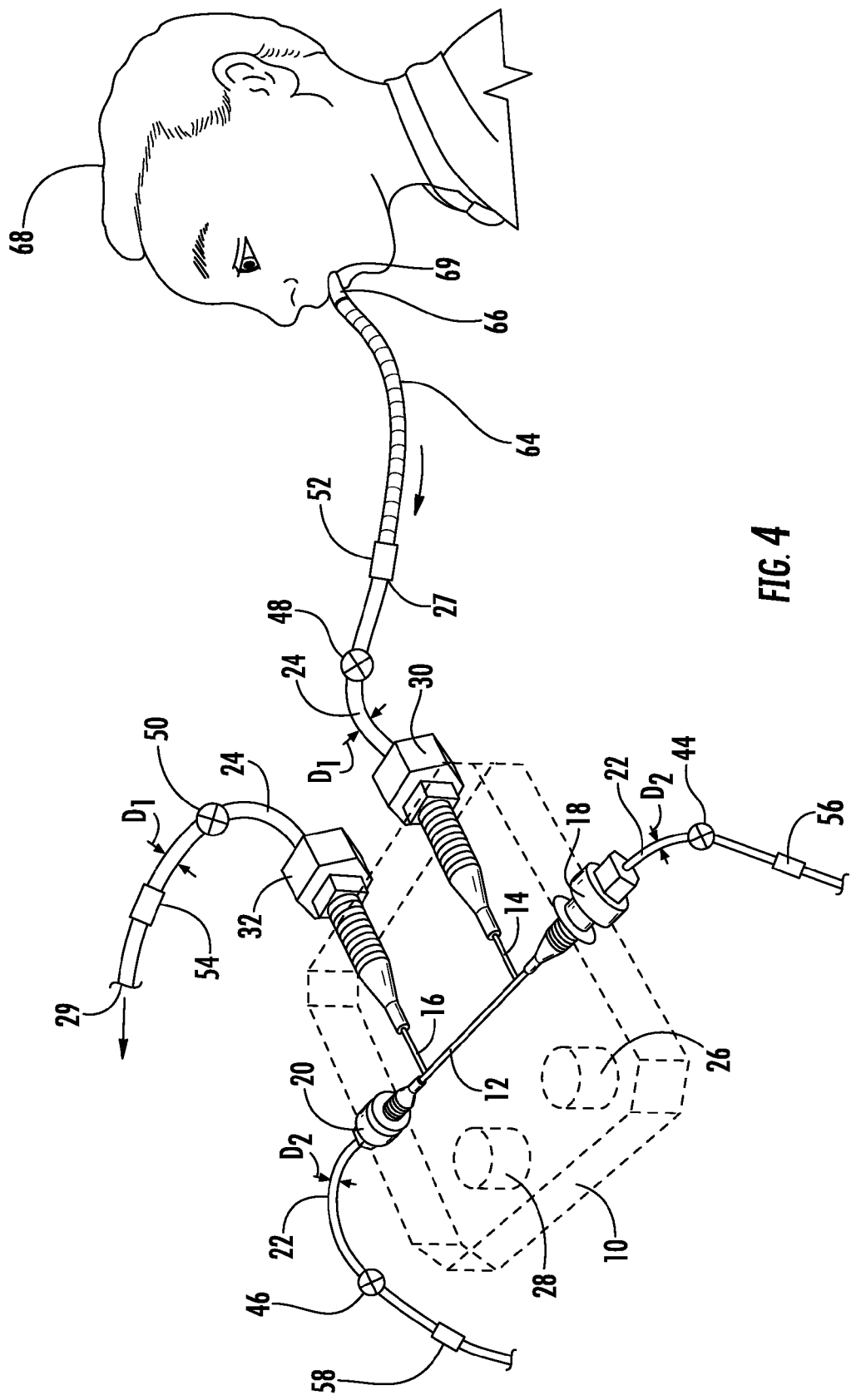
FIG. 4 is a perspective view of the analyte concentrator-microreactor (ACM) device connected to the mouth of a person through a tubing and adapter system to analyze the constituents of exhaled breath.

FIG. 4 illustrates modular and portable analyte concentrator-microreactor (ACM) device 10 connected through tubing 64 and adaptor 66 to mouth 69 of individual 68 exhaling breath constituents to ACM device 10. Alternatively, adaptor 66 can be received over nasal passages or a nipple of an individual. Tubing 64 is connected to transport capillary or passage 24 of ACM device 10 through coupler 52. Transport capillary or passage 24 can have a wider diameter $D_1$ than diameter $D_2$ of separation capillary or passage 22, which facilitates the path of volatile, semi-volatile, and non-volatile breath constituents through transport capillary or passage 24 from inlet end 27 to outlet end 29, passing through inner cavity or channel 12 of analyte concentrator-microreactor (ACM) device 10.

Individual 68 can breathe out or exhale through their mouth 69 a number of substances, resulting in a unique breath signature that contains not only oxygen, nitrogen and carbon dioxide but also volatile organic compounds. Those are chemicals from inside and outside the body that evaporate at room temperature and are the source of most breath odors. Exhaled breath also contains semi-volatile and non-volatile compounds, such as microscopic droplets of proteins, antibodies, peptides, DNA and other chemicals that contain a wealth of additional health information. It may also contain cellular, subcellular, viral and/or vesicular materials or structures.

In order for the breath constituents to pass through analyte concentrator-microreactor (ACM) device 10, micro-valves 44 and 46, controlling the path of fluid through separation capillary or passage 22, must be closed, and micro-valves 48 and 50, controlling the path of fluid through transport capillary or passage 24, must be open. Tubing 64 is connected to transport capillary or passage 24 through coupler 52, and to adaptor 66 introduced into the mouth 69 of individual 68. Inner cavity or channel 12 of analyte concentrator-microreactor (ACM) device 10, contains the appropriate affinity ligands immobilized to the micro-structure or directly to wall 17 of ACM device 10, to capture one or more of the cellular, subcellular, viral, and/or vesicular materials or structures, and/or chemical and biochemical analytes present in breath, either volatile, semi-volatile, or non-volatile.

Breath is a unique bodily fluid; it is available on a continuous basis. The analysis of human and animal breath samples, containing cellular, viral and/or vesicular materials or structures, as well as volatile, semi-volatile, and/or non-volatile organic and inorganic components, promises to be a powerful non-invasive and safe diagnostic tool for detection of many diseases, as well as assessing environmental exposure. Some of the diseases identified by breath analysis include diabetes, heart disease, oxidative stress, gastrointestinal disease, metabolic disorders, active pulmonary tuberculosis, chronic obstructive pulmonary disease (COPD), lung cancer and breast cancer, and in the diagnosis of alcohol intoxication, asthma, heart transplant rejection, *Helicobacter pylori* infection, carbon dioxide poisoning, and lactose intolerance. Similarly, nasal or nasopharyngeal aspirate fluids, and nipple aspirate fluids may also contain cellular, viral, and/or vesicular materials or structures, as well as volatile, semi-volatile, and/or non-volatile organic and inorganic components indicating a particular physiological, physiopathological or toxicological condition. (Cited, and incorporated hereby reference into this application, by Phillips et al., PLoS ONE 9(3): e90226. Doi: 10.1371/journal.pone.0090226, 2014; Minh et al., Diabetes Research and Clinical Practice 2012, 97(2): 195-205; Kim et al., Trends in Analytical Chemistry 2012, 33: 1-8; Boots et al., Journal of Breath Research 2012, 6(2): 027108. Doi: 10.1088/1752-7155/6/2/027108; Lourenco et al., Metabolites 2014, 4: 465-498; Ridgway, Frontiers in Endocrinology 2013 4:152. Doi: 10.3389/fendo.2013.00152; Liang et al., The Scientific World Journal 2012, doi: 10.1100/2012/217518; Kurova et al., Russian Journal of Bioorganic Chemistry 2011, 37(1): 48-52; Cheng et al., Journal of Cancer Therapy 2011, 2: 1-8; Pare et al., Plant Physiology 1999, 121: 325-331; Garcia-Munoz et al., Bioanalysis 2014, 6: 2331-2333; Lewis et al., Clinical and Experimental Allergy 2012, 42: 1734-1744; Miller et al., Biomarker Research 2013, 1: 18-23; Maskarinec et al., Nutrition and Cancer 2013, 65: 1116-1121; Suijkerbuijk et al., Annals of Oncology 2007, 18: 1743-1754; Pawlik et al., BMC Cancer 2006, 6: 68. Doi: 10.1186/1471-2407-6-68; U.S. Pat. Nos. 8,871,521; 8,834,798; 8,747,325; 8,663,581; 8,211,035; and 2013/0253358.

Although it has been demonstrated the potential of using breath samples for specific biomarkers of different diseases, still the bottleneck is sample collection which is prone to sources of errors, including chemical contamination and some limitations in the optimization of the collection conditions, such as efficient condensation of breath by a controlled temperature to obtain exhale breath condensate. Furthermore, the analysis of the collected potential biomarker analytes can be time-consuming, not capable of providing enough detection sensitivity, and expensive. Also, the evaluation of the results obtained from breath analysis using different approaches, still remains insufficient because of the lack of standardized procedures and poor methods of validation.

The analyte concentrator-microreactor (ACM) device 10 provides an easy, rapid, reliable, and accurate method to capture cellular, viral, and/or vesicular materials or structures, as well as volatile, semi-volatile, and non-volatile substances present in exhaled breath that can serve as indicators or biomarkers of a single or multiple diseases or toxic states. One or more affinity ligands with restricted or broad specificity for capturing analytes in breath samples can be immobilized to a matrix localized within inner cavity or channel 12 of analyte concentrator-microreactor (ACM) device 10 or directly to wall 17 of ACM device 10. Analyte concentrator-microreactor (ACM) device 10 can be subjected to temperature control, as well as the entire tubing system connecting ACM device 10 to mouth 69, referred to as transport capillary or passage 24 and tubing 64. Such control of temperature can facilitate the path of exhaled breath from the mouth to outlet end 29 of transport capillary or passage 24, and to facilitate the binding of substances in the exhaled breath to the one or more affinity ligands immobilized within ACM device 10. In order to facilitate and maintain a uniform flow of exhaled breath throughout tubing 64 until outlet end 29 of transport capillary or passage 24 a controlled speed miniaturized vacuum pump 82 can be installed at exit 87 of transport capillary or passage 24 as shown in FIG. 5.

Analyte concentrator-microreactor (ACM) device 10 is portable and can be brought to a patient's bedside or it can be mailed by a patient to a central diagnostic laboratory after the specimen collection is facilitated by an appropriate kit. Micro-valves 44, 46, 48, and 50 can facilitate the residence time of the substances in the exhaled breath within ACM device 10, until ACM device 10 is mounted and installed onto the cartridge-cassette to further analyze the bound and released biomarker analytes by capillary electrophoresis or any other analytical separation instrument.

Figure 5:
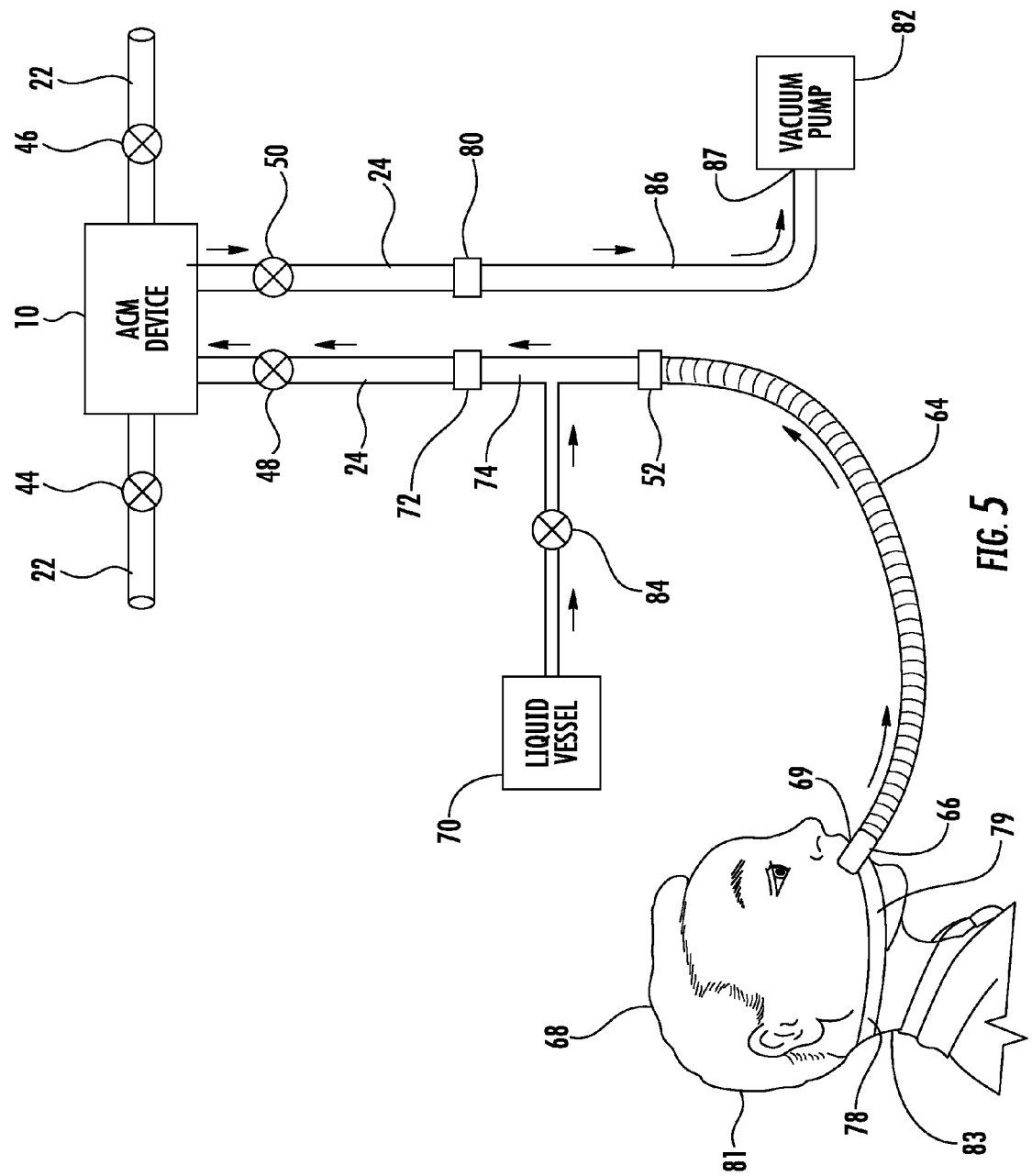
FIG. 5 is a perspective view of the analyte concentrator-microreactor (ACM) device connected to the mouth of a person through a tubing system to analyze the constituents of exhaled breath, with the help of a vacuum pump using a controlled vacuum aspiration flow, and the introduction of a buffer or solution to facilitate the uniform operation of the system. Additionally, the solution can contain a derivatizing agent to derivatize the analytes of interest, and thus facilitating the binding to the affinity ligands immobilized within the ACM device and the enhancement of their detection.

FIG. 5 illustrates modular and portable analyte concentrator-microreactor (ACM) device 10 connected through tubing 64 and adaptor 66 to mouth 69 of individual 68 exhaling volatile, semi-volatile, and non-volatile breath constituents from exhaled breath or exhaled breath condensate, including organic and inorganic compounds, bacteria, viruses, fungi, other microorganisms, allergens, cellular and non-cellular particles, and globules to ACM device 10. Tubing 64 is connected to inlet end 27 (FIGS. 1, 2, and 3) of transport capillary or passage 24 through T-connector tube 74 and couplers 52 and 72. Outlet end 29 (FIGS. 1, 2, and 3) of transport capillary or passage 24 can be connected directly to a vacuum pump 82 or through connector 80 connecting connector tube 86 to vacuum pump 82 at exit 87. T-connector tube 74 couples tubing 64 to inlet end 27 (FIGS. 1, 2, and 3) of transport capillary or passage 24, and to liquid container or vessel 70. The flow of liquid from liquid vessel or container 70 is controlled by micro-valve 84. Fastener device system 78 helps to maintain in position tubing 64 to mouth 69 of individual 68 through adaptor 66. Fastener devices system 78 can include band 79. Band 79 extends around head 81 or neck 83 of individual 68 and is connected to adapter 66. Individual 68 can be a person or animal.

Many volatile, semi-volatile, and non-volatile compounds may be difficult to extract from a fluid, in particular when derived from biological and non-biological fluids. Some of these compounds fall into different chemical classes, such as acidic, basic, neutral, halogenated, oxygenated, polar, non-polar, low-boiling, and high-boiling compounds. Liquid container or vessel 70 provides to the system an appropiate buffer or solution in order to perform the capturing step in ACM device 10 in liquid. The buffer or solution contained in liquid vessel or container 70 may also have a derivatizing compound to derivatize or tag one or more specific chemical groups of the analytes of interest present in the breath exhale.

Derivatization is a technique used in chemistry which transforms a chemical compound into a product of similar chemical structure, called a derivative. The derivative in general has different chemical properties than the underivatized analyte of interest. It may have different solubility, reactivity, boiling point, melting point, aggregate state, etc. The derivatized analyte of interest may also facilitate the binding to one or more affinity ligands immobilized to analyte concentrator-microreactor (ACM) device 10, and enhance its detectability by using an appropriate detector.

Vacuum pump 82 can generate a controllable vacuum maintaining a uniform flow from the collecting area of exhaled breath starting at mouth 69 with adaptor 66 to outlet end 29 of transport capillary or passage 24. For transport of exhaled breath to occur under optimal conditions, adaptor 66 must be well positioned in mouth 69 with the help of fastener system device 78. Micro-valves 44 and 46 must be closed, and micro-valves 48 and 50 must be open. Once the aspiration system is working smoothly, micro-valve 84 is open to allow the buffer or solution in liquid vessel or container 70 to enter at T-connector tube 74, where the mixing of cellular, subcellular, viral and/or vesicular structures or materials, and/or chemical or biochemical materials of the exhaled breath with the liquid will occur. The liquid buffer or solution may contain one or more types of detergents and/or other additives to facilitate dissolution of viscous samples or samples containing solid mass. Similar conditions may apply for the processing of nasal and nasopharyngeal aspirate fluids, airway secretions, nipples aspirate fluids, and fluids derived from washes, lavages, and other aspirates. Vacuum pump 82 may have a trap system (FIG. not shown) used as a waste reservoir or container for the excess amount of breath exhale containing also the material that did not bind to ACM device 10.

Fastener system device 78 helps to maintain tubing 64 through adaptor 66 in a steady and fixed position on mouth 69 to allow a uniform entrance of exhaled breath into tubing 64. This may be important in certain cases, when the person may be incapacitated or ill, a baby or young person, or an animal, if the analysis of exhaled breath will help in the diagnosis and prognosis a disease.

Once the sample has been properly collected, micro-valves 48, 50 and 84 can be closed and tubing 64 and tubing 86 connecting to vacuum pump 82 can be disconnected from couplers 72 and 80. Analyte concentrator-microreactor (ACM) device 10 can then be mounted onto the cartridge-cassette and connected to separation capillary 22 to be subjected to the washing process to eliminate excess amount of exhaled breath and non-specifically bound material as shown in FIG. 2. The last step is to apply the appropriate buffer or solution within the separation capillary with micro-valves 44 and 46 open, and micro-valves 48 and 50 closed, followed by a plug of an elution buffer or solution to start the elution and separation process by any of the various modes of capillary electrophoresis. Because of the modular and portable nature of analyte concentrator-microreactor (ACM) device 10, it can be used in the field, in remote locations, in doctor's office, in ambulances, or brought directly to the location of the patient or animal. Sample collection can also be performed at patient's bedside and collected specimen can be mailed to a central diagnostic laboratory.

This invention can also be helpful to determine the presence of volatile, semi-volative and non-volatile organic compounds in samples other than biological fluids, such as aqueous, soil and air samples by capturing the analytes of interest by one or more affinity ligands with high or low binding specificity. The integrated system can also be adapted to work with instruments other than capillary electrophoresis, such as gas chromatography and liquid chromatography.

This invention can also be adapted to collect and analyze volatile, semi-volatile, and non-volatile organic and inorganic compounds emitted by or extracted from flowers, plants, allergens, food or materials that may be of relevance to the fragrance and flavor industries, textile and/or coloring industries, and environmental pollution agencies, and of compounds derived from skin emanations. Furthermore, this invention can be adapted to collect cellular, sub-cellular, viral and vesicular materials or structures, as well as organic and inorganic compounds present in nasal aspirate fluids, nasopharyngeal aspirate fluids, airway secretions, nasal wash, nipple aspirate fluids, and other lavage fluids.

It is understood that the above-described embodiments are illustrative of only a few of the many possible specific embodiments, which can represent applications of the principles of the invention. Numerous and varied other arrangements can be readily devised in accordance with these principles by those skilled in the art departing from the spirit and scope of the invention.

What is claimed is:

1. An integrated unit comprising:
a portable modular analyte concentrator-microreactor (ACM) device;
an inlet transport capillary or passage connected to the analyte concentrator-microreactor (ACM) device;
an outlet transport capillary or passage connected to the analyte concentrator-microreactor (ACM) device;
a separation capillary or passage connected to the analyte concentrator-microreactor (ACM) device;
the separation capillary or passage having an inlet end and an outlet end;
the analyte concentrator-microreactor (ACM) device having a transport inlet port and a transport outlet port connected respectively to the inlet transport capillary or passage and the outlet transport capillary or passage, such that the inlet transport capillary or passage and the outlet transport capillary or passage are positioned in a parallel configuration to each other;
the analyte concentrator-microreactor (ACM) device having a separation inlet port and a separation outlet port connected respectively to the inlet end and the outlet end of the separation capillary or passage;
the analyte concentrator-microreactor (ACM) device having an internal passage or channel which includes an elongated concentration area connecting the separation inlet port to the separation outlet port;
the inlet transport capillary or passage and the outlet transport capillary or passage, positioned in the parallel configuration to each other, intersect the elongated concentration area at two separate points between the separation inlet port and separation outlet port to form an analyte concentrator-microreactor area;
the elongated concentration area of the analyte concentrator-microreactor (ACM) device providing a place of shelter for received microstructures or a matrix assembly and/or provides a place of shelter for encapsulated cellular and/or subcellular structures, and/or cellular receptors;
one or more affinity ligands can be immobilized on the microstructures or the matrix assembly localized within the elongated concentration area of the analyte concentrator-microreactor (ACM) device for generating a concentration space where concentration of one or more analytes of interest and/or their respective modified and/or altered corresponding molecular counterpart from a sample introduced into the inlet transport capillary or passage occurs and/or for generating a microreaction space where microreaction of the one or more analytes of interest and/or their respective modified and/or altered corresponding molecular counterpart from the sample introduced into the inlet transport capillary or passage occurs;
alternatively the one or more affinity ligands can be immobilized directly to an internal wall of a cavity or channel forming the elongated concentration area of the analyte concentrator-microreactor (ACM) device without the need of the microstructures or the matrix assembly;
controlling means for independently controlling flow of the sample or buffers in the transport capillaries or passages and past the analyte concentrator-microreactor (ACM) device and conveyed by electromigration, electro-osmotic flow, mechanical pressure or a combination of electro-osmotic flow and mechanical pressure to an outlet end of the outlet transport capillary or passage, and for separately and independently controlling flow of a separation buffer supply, eluting buffer supply or cleaning buffer supply through the separation capillary or passage and past the analyte concentrator-microreactor (ACM) device and conveyed by electromigration, electro-osmotic flow, mechanical pressure or a combination of electro-osmotic flow and mechanical pressure to the outlet end of the separation capillary or passage; and
an interchangeable cartridge-cassette or interchangeable unit to which the ACM device is detachably mounted using couplers to the inlet and outlet ends of the separation capillary or passage of the cartridge-cassette unit,
a detection system can be positioned in operation with a monitoring area of the separation capillary or passage;
wherein the portable modular analyte concentrator-microreactor (ACM) device can capture, isolate, purify, concentrate and separate analytes of interest and/or their respective modified and/or altered corresponding molecular counterpart bound to and released from the analyte concentrator-microreactor (ACM) device by alternating fluid communication of the separation buffer supply and then the eluting buffer supply and delivering the released analytes of interest and/or their respective modified and/or altered corresponding molecular counterpart to the detection system or a detection system of an analytical separation instrument separately, independently and sequentially by electromigration, electro-osmotic flow, mechanical pressure or a combination of electro-osmotic flow and mechanical pressure within the separation capillary or passage and the detection system providing quantitation, identification, and/or characterization information of the separated analytes.

2. The integrated unit of claim 1 wherein the microstructures or matrix assembly within the elongated concentration area of the analyte concentrator-microreactor (ACM) device have a surface or a wall to which one or more affinity ligands are immobilized.

3. The integrated unit of claim 1 wherein the matrix assembly within the elongated concentration area of the analyte concentrator-microreactor (ACM) device includes a plurality of the microstructures.

4. The integrated unit of claim 1 wherein the matrix assembly within the elongated concentration area of the analyte concentrator-microreactor (ACM) device is free-floating, and the analyte concentrator-microreactor area retains the free-floating matrix assembly by pressure-resistant porous end walls or frits disposed at the inlet and outlet ports of the transport capillaries or passages and the separation capillary or passage.

5. The integrated unit of claim 1 wherein the matrix assembly within the elongated concentration area of the analyte concentrator-microreactor (ACM) device is free-floating, and the analyte concentrator-microreactor area retains the free-floating matrix assembly by the elongated concentration area having a constricted area or a diameter of the internal passage or channel being larger than a diameter of the separation capillary or passage.

6. The integrated unit of claim 1 wherein the matrix assembly within the elongated concentration area of the analyte concentrator-microreactor (ACM) device is free-floating, and the analyte concentrator-microreactor area retains the free-floating matrix assembly, wherein said free-floating matrix assembly comprises metal chemical groups of micro or nano size or a metallic material and a magnet is associate with the elongated concentration area.

7. The integrated unit of claim 1 wherein the matrix assembly within the elongated concentration area of the analyte concentrator-microreactor (ACM) device includes a fixed architecture defined by beaded microstructures interconnected to each other and to the internal wall of the cavity or channel forming the elongated concentration area of the analyte concentrator-microreactor (ACM) device.

8. The integrated unit of claim 1 wherein the matrix assembly within the elongated concentration area of the analyte concentrator-microreactor (ACM) device includes sol-gel or monoliths which are supports having a single, continuous piece of porous materials, nanoparticles and/or nanocomposites.

9. The integrated unit of claim 1 wherein the affinity ligands immobilized on a surface of the microstructures within the elongated concentration area of the analyte concentrator-microreactor (ACM) device or a surface of the internal wall of the cavity or channel forming the elongated concentration area of the analyte concentrator-microreactor (ACM) device are immobilized by physicochemical interactions or by covalent chemical interactions.

10. The integrated unit of claim 1 wherein the affinity ligands immobilized to a surface of the microstructures or the matrix assembly within the elongated concentration area of the analyte concentrator-microreactor (ACM) device or immobilized directly to a surface of the internal wall of the cavity or channel forming the elongated concentration area of the analyte concentrator-microreactor (ACM) device include biological and non-biological affinity ligands, selected from the group consisting of intact polyclonal or monoclonal antibodies, single-chain antibodies, antibody fragments, antibody-drug conjugates, organic and inorganic compounds, antigens, protein A, protein G, protein A/G, protein L, lectins, glycoproteins, glycolipids, enzymes, substrates, cofactors, coenzymes, drugs, drug metabolites, vitamins, hormones, proteins, peptides, viruses, cells, subcellular structures, cellular organelles or components, cell-derived vesicles, globules, prions, receptors, membranes, DNA, RNA, polynucleotides, aptamers, dyes, ions, ligands with metal-containing moieties, ligands with organometallic-containing moieties, ligands with hydrophobic-containing moieties, ligands with hydrophilic-containing moieties, ligands with mixed-mode-containing moieties, alumina, activated charcoal, recombinant ligands, and synthetic ligands.

11. The integrated unit of claim 1 wherein the analytes of interest and/or their respective modified and/or altered corresponding counterpart include biological and non-biological analytes to be captured, isolated, and concentrated from the microstructures or matrix assembly containing intact antibodies, antibody fragments, antibody-drug conjugates, organic and inorganic compounds, antigens, protein A, protein G, lectins, glycoproteins, glycolipids, enzymes, substrates, cofactors, coenzymes, drugs, drug metabolites vitamins, hormones, proteins, peptides, viruses, circulating and non-circulating cells, cellular organelles or components, cell-derived vesicles, globules, prions, bacterial cells, receptors, membranes, dyes, DNA, RNA, polynucleotides, aptamers, ions, metal-containing moieties, organometallic moieties, synthetic ligands, metabolites, and various altered or modified molecular entities.

12. The integrated unit of claim 1 wherein the at least one or more affinity ligands immobilized to a surface of the microstructures or matrix assembly within the elongated concentration area of the analyte concentrator-microreactor (ACM) device or immobilized directly to a surface of the internal wall of the cavity or channel forming the elongated concentration area of the analyte concentrator-microreactor (ACM) device is capable of performing a reversible affinity capture reaction with the one or more analytes of interest and/or their respective modified and/or altered corresponding molecular counterpart present in the sample.

13. The integrated unit of claim 1 wherein at least one or more affinity ligands immobilized to a surface of the microstructures or matrix assembly retained within the elongated concentration area of the analyte concentrator-microreactor (ACM) device or immobilized directly to a surface of the internal wall of the cavity or channel forming the elongated concentration area of the analyte concentrator-microreactor (ACM) device is capable of performing one chemical or biochemical reaction with the one or more analytes of interest and/or their respective modified and/or altered corresponding molecular counterpart present in the sample.

14. The integrated unit of claim 13 wherein the at least one chemical or biochemical reaction carried out within a cavity or channel forming the elongated concentration area of the analyte concentrator-microreactor (ACM) device includes peptide synthesis, nucleic acid synthesis, synthesis of organic and inorganic compounds, sequencing of proteins or biopolymers or an enzymatic reaction.

15. The integrated unit of claim 1 wherein the analyte concentrator-microreactor area of the analyte concentrator-microreactor (ACM) device has the encapsulated cellular and/or subcellular structures localized and retained therein.

16. The integrated unit of claim 1 wherein the encapsulated cellular or subcellular structures localized and retained within the analyte concentrator-microreactor area of the analyte concentrator-microreactor (ACM) device are adapted to perform metabolic studies.

17. The integrated unit of claim 1 wherein the analyte concentrator-microreactor area of the analyte concentrator-microreactor (ACM) device has the cellular receptors localized and retained therein.

18. The integrated unit of claim 1 wherein the cellular receptors localized and retained within the analyte concentrator-microreactor area of the analyte concentrator-microreactor (ACM) device are adapted to perform bioactivity studies.

19. The integrated unit of claim 1 wherein the analyte concentrator-microreactor (ACM) device has an acoustic micromixing system.

20. The integrated unit of claim 1 wherein the analyte concentrator-microreactor (ACM) device has a microwave pulse system.

21. The integrated unit of claim 1 wherein the analyte concentrator-microreactor (ACM) device has a temperature control system.

22. The integrated unit of claim 1 wherein connecting points of the transport capillaries or passages and the separation capillary or passage to the analyte concentrator-microreactor (ACM) device are hermetically sealed.

23. The integrated unit of claim 1 wherein the controlling means for independently controlling flow comprises microvalves operated manually or by electronic-controlled circuitry, the electronically-controlled circuitry adapted to be operated by a smartphone.

24. The integrated unit of claim 1 wherein the controlling means controls the operation of a cleaning buffer fluid means for introducing the cleaning buffer supply, optimization buffer fluid means for introducing an optimization buffer, sample fluid means for introducing a sample fluid, and washing buffer fluid means for introducing a washing buffer fluid through the inlet transport capillary or passage.

25. The integrated unit of claim 24 wherein the controlling means controls the operation of the cleaning buffer fluid means, the optimization buffer fluid means, a separation buffer fluid means for introducing the separation buffer supply through the separation capillary or passage, and followed by a plug of the eluting buffer supply for introducing the plug of the eluting buffer supply to release the analytes bound to the analyte concentrator-microreactor (ACM) device.

26. The integrated unit of claim 1 wherein the functional operation of the integrated unit, containing the portable modular analyte concentrator-microreactor (ACM) device, when connected to the analytical separation instrument, and/or the detection system is carried out in a coordinated fashion through an electronically-controlled circuitry of a complete integrated unit, the electronically-controlled circuitry adapted to be operated by a smartphone.

27. The integrated unit of claim 1 wherein the analytical separation instrument is a capillary electrophoresis instrument, a low-pressure liquid chromatography instrument, a high-performance liquid chromatography instrument, a ultra-pressure high-performance liquid chromatography instrument, a nano high-performance liquid chromatography instrument, a gas chromatography instrument, or a modified version of these instruments.

28. The integrated unit of claim 1 wherein the detection system comprises one or more detectors of on-line and/or off-line detector types, including ultraviolet, fluorescence, laser-induced fluorescence, mass spectrometer, nuclear magnetic resonance, circular dichroism, electrochemical, conductivity, charged coupled device (CCD), chemiluminescence, bioluminescence radioactive, and/or modified versions of these detectors.

29. The integrated of claim 1 wherein the separation capillary or passage is filled with an electrically conductive fluid that is used for separation of the captured, isolated, purified, concentrated, and released analytes of interest, and also preserves the integrity of the immobilized affinity ligands localized at the analyte concentrator-microreactor (ACM) device.

30. The integrated unit of claim 1 wherein the separation capillary or passage is filled with a liquid gel matrix containing an electrically conductive fluid that is used for separation of the captured, isolated, purified, concentrated, and released analytes of interest, and also preserves the integrity of the immobilized affinity ligands localized at the analyte concentrator-microreactor (ACM) device.

31. The integrated unit of claim 25 wherein the plug of the eluting buffer or solution used to release the analyte of interest bound to the analyte concentrator-microreactor (ACM) device contains an organic solvent, a chaotropic agent, a high salt buffer, a low pH buffer, a high pH buffer, a detergent, an additive to facilitate dissolution of the sample, a structurally-related analog substance competing for the binding site of the analyte of interest, or a combination of them and/or a chromophoric substance.

32. The integrated unit of claim 1 wherein the analyte concentrator-microreactor (ACM) device is color-coded to represent the presence of specific affinity ligands and/or a particular functionality,
wherein the analyte concentrator-microreactor (ACM) device is used for the determination of a certain number of analyte biomarkers associated to the diagnosis and/or prognosis of a particular disease or toxic state, and/or to identify the normality-abnormality of a certain organ, tissue, cluster cells, circulating cells, or circulating, cell-derived vesicle operation and/or application.

33. The integrated unit of claim 1 wherein if separation of analytes occurs by capillary electrophoresis, the separation can be carried out by one or more or a combination of any of modes of capillary electrophoresis.

34. The integrated unit of claim 1 wherein the controlling means comprises a micro-valve system operatively associated with the transport capillaries or passages and the separation capillary or passage for independently controlling the flow of the sample in the transport capillaries or passages and separately and independently forming a microenvironment in the elongated concentration area of the analyte concentrator-microreactor (ACM) device to mix reagents to optimize the binding and capture of the one or more analytes of interest and/or their respective modified and/or altered corresponding molecular counterpart.

35. The integrated unit of claim 34 wherein the micro-valve system includes micro-valves which are motor operated and remotely controlled by a processor based on a predetermined set of instructions.

36. The integrated unit of claim 34 wherein the micro-valve system includes micro-valves which are manually operated.

37. The integrated unit of claim 1 wherein the analyte concentrator-microreactor (ACM) device and the connected transport capillaries or passages and the separation capillary or passage has a temperature control system generated by air or a dry system not involving liquid.

38. The integrated unit of claim 1 wherein the analyte concentrator-microreactor (ACM) device and the connected transport capillaries or passages and the separation capillary or passage has a temperature control system generated by a liquid system surrounding the transport and separation passages.

39. The integrated unit of claim 1 wherein the transport capillaries or passages and the separation capillary or passage are connected to the analyte concentrator-microreactor (ACM) device through a micro-valve and connector for each of the four inlet-outlet ports respectively of the transport capillaries or passages and the separation capillary or passage of the analyte concentrator-microreactor (ACM) device.

40. The integrated unit of claim 1 wherein the analyte concentrator-microreactor (ACM) device is mounted to the interchangeable cartridge-cassette or the interchangeable unit by a detachable support means forming a single integrated modular entity.

41. The integrated unit of claim 40 wherein the support means is one or more supports attached to the interchangeable cartridge-cassette, the one or more supports being received in a respective aperture in the analyte concentrator (ACM) device.

42. The integrated unit of claim 1 wherein the analyte concentrator (ACM) device and the interchangeable cartridge-cassette are manufactured as a single integrated modular unit.

43. The integrated unit of claim 1 wherein the detection system comprises a detector selected from the group consisting of ultraviolet, fluorescence, laser-induced fluorescence, nuclear magnetic resonance, electrochemical, conductivity, chemiluminescence, bioluminescence, circular dichroism, charged coupled device (CCD), radioactive, and mass spectrometer detection systems.

44. The integrated unit of claim 1 wherein the analytes of interest and/or their respective modified and/or altered corresponding counterpart include biological and non-biological analytes present in simple and complex matrices, selected from the group consisting of intact antibodies, antibody fragments, antigens, protein A, protein G, lectins, glycoproteins, glycolipids, enzymes, substrates, cofactors, coenzymes, drugs, vitamins, hormones, proteins, viruses, cells, subcellular structures, cellular organelles or components, cell-derived vesicles, globules, prions, receptors, membranes, dyes, metal-containing moieties, organometallic moieties, and synthetic ligands.

45. The integrated unit of claim 1 further comprising:
tubing removably coupled to an inlet end of the inlet transport capillary or passage and an adaptor coupled or integral with the tubing, wherein the adaptor is adapted for receiving exhaled breath or exhaled breath condensate, or released volatile, semi-volatile organic and/or inorganic emitted from or by an individual.

46. The integrated unit of claim 45 wherein the tubing is coupled with a first tubing coupler to the inlet end of the inlet transport capillary or passage.

47. The integrated unit of claim 46 wherein the first tubing coupler is connected to a first end of a T connector tube, a second end of the T connector tube is connected to a second tubing coupler, the second tubing coupler is coupled to the inlet end of the inlet transport capillary or passage, a base end of the T connector tube is connected to a liquid container or vessel.

48. The integrated unit of claim 47 further comprising a micro-valve positioned between the base end of the T-connector tube and said liquid container or vessel.

49. The integrated unit of claim 45 wherein a diameter of said transport capillaries or passages is larger than a diameter of said separation capillary or passage.

50. The integrated unit of claim 45 further comprising:
a vacuum pump connected to the outlet end of said outlet transport capillary or passage.

51. The integrated unit of claim 45 further comprising a fastener device system connected to said adaptor, said fastener device system adapted for maintaining in position said adaptor in a mouth of the individual.

52. The integrated unit of claim 45 wherein the analyte concentrator (ACM) device and the tubing has a temperature control system.

53. The integrated unit of claim 1 further comprising:
tubing removably coupled to the inlet end of the inlet transport capillary or passage and an adaptor coupled or integral with the tubing, wherein the adaptor is adapted for receiving exhaled or released volatile, semi-volatile, and non-volatile organic and/or inorganic compounds emitted by or extracted from plants, flowers, skin emanations, allergens, or food.

54. The integrated unit of claim 1 further comprising:
tubing removably coupled to the inlet end of the inlet transport capillary or passage and an adaptor coupled or integral with the tubing, wherein the adaptor is adapted for receiving bacteria; viruses; fungi; microorganisms; allergens; globules; spores; cellular, subcellular, viral and/or vesicular materials or structures; and/or organic and inorganic compounds present in human and animal exhaled breath, exhaled condensate, nasal aspirate fluid, nasopharyngeal aspirate fluid, airway secretions, saliva, nipple aspirate fluid, washes or lavages.

55. An integrated unit comprising:
a portable modular analyte concentrator-microreactor (ACM) device;
an inlet transport capillary or passage connected to the analyte concentrator-microreactor (ACM) device;
an outlet transport capillary or passage connected to the analyte concentrator-microreactor (ACM) device;
a separation capillary or passage connected to the analyte concentrator-microreactor (ACM) device;
the separation capillary or passage having an inlet end and an outlet end;
the analyte concentrator-microreactor (ACM) device having a transport inlet port and a transport outlet port connected respectively to the inlet transport capillary or passage and the outlet transport capillary or passage, such that the inlet transport capillary or passage and the outlet transport capillary or passage are positioned in a parallel configuration to each other;
the analyte concentrator-microreactor (ACM) device having a separation inlet port and a separation outlet port connected respectively to the inlet end and the outlet end of the separation capillary or passage;
the analyte concentrator-microreactor (ACM) device having an internal passage or channel which includes an elongated concentration area connecting the separation inlet port to the separation outlet port;
the inlet transport capillary or passage and the outlet transport capillary or passage, positioned in the parallel configuration to each other, intersect the elongated concentration area at two separate points between the separation inlet port and separation outlet port to form an analyte concentrator-microreactor area;
the elongated concentration area the one analyte concentrator-microreactor (ACM) device providing a place of shelter for received microstructures or a matrix assembly and/or provides a place of shelter for encapsulated cellular and/or subcellular structures, and/or cellular receptors;
one or more affinity ligands can be immobilized to the microstructures or the matrix assembly localized within the elongated concentration area of the analyte concentrator-microreactor (ACM) device for generating a concentration space where concentration of one or more analytes of interest and/or their respective modified and/or altered corresponding molecular counterpart from a sample introduced into the inlet transport capillary or passage occurs and/or for generating a microreaction space where microreaction of the one or more analytes of interest and/or their respective modified and/or altered corresponding molecular counterpart from the sample introduced into the inlet transport capillary or passage occurs;
alternatively the one or more affinity ligands can be immobilized directly to an internal wall of a cavity or channel forming the elongated concentration area of the analyte concentrator-microreactor (ACM) device without the need of the microstructures or the matrix assembly;
controlling means for independently controlling flow of the sample or buffers in the transport capillaries or passages and past the analyte concentrator-microreactor (ACM) device and conveyed by electromigration, electro-osmotic flow, mechanical pressure or a combination of electro-osmotic flow and mechanical pressure to an outlet end of the outlet transport capillary or passage, and for separately and independently controlling flow of a separation buffer supply, eluting buffer supply or cleaning buffer supply through the separation capillary or passage and past the analyte concentrator-microreactor (ACM) device and conveyed by electromigration, electro-osmotic flow, mechanical pressure or a combination of electro-osmotic flow and mechanical pressure to the outlet end of the separation capillary or passage;

tubing removably coupled to an inlet end of the inlet transport capillary or passage and an adaptor coupled or integral with the tubing, the adaptor is adapted for receiving breath, exhaled breath condensate, nasal aspirate fluid, nasopharyngeal aspirate fluid, airway secretions, nipple aspirate fluid, or other aspirate fluids, washes or lavages from an individual; and an interchangeable cartridge-cassette or interchangeable unit to which the ACM device is mounted using couplers to the inlet end and the outlet end of the separation capillary or passage of the interchangeable cartridge-cassette unit, a detection system can be positioned in operation with a monitoring area of the separation capillary or passage;

wherein the modular analyte concentrator-microreactor (ACM) device can capture, isolate, purify, concentrate and separate analytes of interest and/or their respective modified and/or altered corresponding molecular counterpart bound to and released from the analyte concentrator-microreactor (ACM) device by alternating fluid communication of the separation buffer supply and then the eluting buffer supply and delivering the released analytes of interest and/or their respective modified and/or altered corresponding molecular counterpart to the detection system or a detection system of a capillary electrophoresis instrument or other analytical separation instrument separately, independently and sequentially by electromigration, electro-osmotic flow, mechanical pressure or a combination of electro-osmotic flow and mechanical pressure within the separation capillary or passage.

* * * * *